United States Patent
Reichmann et al.

(10) Patent No.: US 8,680,018 B2
(45) Date of Patent: *Mar. 25, 2014

(54) SELECTION SYSTEM

(75) Inventors: Lutz Reichmann, Cambridge (GB); Peter Kristensen, Tranbjerg (DK); Jean-Luc Jestin, Paris (FR); Gregory Paul Winter, Cambridge (GB)

(73) Assignee: Domantis Limited, Brentford, Middlesex (GB)

( * ) Notice: Subject to any disclaimer, the term of this patent is extended or adjusted under 35 U.S.C. 154(b) by 383 days.

This patent is subject to a terminal disclaimer.

(21) Appl. No.: 12/246,741

(22) Filed: Oct. 7, 2008

(65) Prior Publication Data
US 2009/0203542 A1 Aug. 13, 2009

Related U.S. Application Data

(63) Continuation of application No. 09/710,444, filed on Nov. 10, 2000, now Pat. No. 7,442,159, which is a continuation of application No. PCT/GB99/01526, filed on May 13, 1999.

(30) Foreign Application Priority Data

May 13, 1998 (GB) .................................. 9810223.9
May 13, 1998 (GB) .................................. 9810228.8

(51) Int. Cl.
*C40B 30/06* (2006.01)
(52) U.S. Cl.
USPC ....................................................... 506/10
(58) Field of Classification Search
None
See application file for complete search history.

(56) References Cited

U.S. PATENT DOCUMENTS

| 5,223,409 A | 6/1993 | Ladner et al. |
| 5,432,018 A | 7/1995 | Dower et al. |
| 5,849,500 A | 12/1998 | Breitling et al. |

FOREIGN PATENT DOCUMENTS

| WO | WO90/05144 | 5/1990 | ............. C07K 13/00 |
| WO | WO90/14430 | 11/1990 | ............. C12P 19/34 |
| WO | WO92/01047 | 1/1992 | ............. C12N 15/00 |
| WO | WO92/20791 | 11/1992 | ............. C12N 15/00 |
| WO | WO93/11236 | 6/1993 | ............. C12N 15/13 |

OTHER PUBLICATIONS

Stengele (Mar. 5, 1990) Journal of Molecular Biology vol. 212 pp. 143 to 149.*
Matthews (May 21, 1993) Science vol. 260 pp. 1113 to 1117.*
Fontana (Apr. 1, 1997) Folding and Design vol. 2 pp. R17 to R26.*
Riechmann (Jul. 25, 1997) Cell vol. 90 pp. 351 to 360.*
Krebber (1997) Journal of Molecular Biology vol. 268 pp. 607 to 618.*
Rubingh, D.N. (1997). Protein engineering from a bioindustrial point of view. *Current Opinion in Biotechnology*. 8, 417-422.
Fersht, A.R. (1993). Protein folding and stability: the pathway of folding of barnase. *FEBS Letters*. 325, 5-16.

(Continued)

*Primary Examiner* — Christian Boesen
(74) *Attorney, Agent, or Firm* — Jason C. Fedon; William T. Han

(57) ABSTRACT

The present invention concerns a method for the selection of a virus comprising the steps of: (a) providing a virus encoding and displaying a fusion polypeptide, said fusion polypeptide comprising a heterologous polypeptide inserted into the sequence of a viral coat protein polypeptide, wherein said virus comprises a cleavable site located within a displayed polypeptide; (b) exposing the virus to a cleaving agent; (c) propagating the virus comprising intact fusion protein.

2 Claims, 6 Drawing Sheets

(56) References Cited

OTHER PUBLICATIONS

Zhao, H., et al. (1998). Molecular evolution by staggered extension process (StEP) in vitro recombination. *Nature Biotechnology*. 16, 258-261.
Patten, P.A., R.J. Howard, and W.P.C. Stemmer (1997). Applications of DNA shuffling to pharmaceuticals and vaccines. *Current Opinion in Biotechnology*. 8, 724-733.
Sauer, R.T. (1996). Protein folding from a combinatorial perspective. *Folding & Design*. 1, R27-R30.
Dahiyat, B.I., C.A. Sarisky, and S.L. Mayo. (1997). De Novo Protein Design: Towards Fully Automated Sequence Selection. *Journal of Molecular Biology*. 273, 789-796.
Riddle, D.S., et al. (1997). Functional rapidly folding proteins from simplified amino acid sequences. *Nature Structural Biology*. 4(10), 805-809.
Hoogenboom, H.R. and G. Winter. (1992). By-passing Immunisation. Human Antibodies from Synthetic Repertoires of Germline VH Gene Segments Rearranged in Vitro. *Journal of Molecular Biology*. 227, 381-388.
Winter, G., et al. (1994). Making Antibodies by Phage Display Technology. *Annual Review of Immunology*. 12, 433-455.
Braisted, A.C. and J.A. Wells. (1996). Minimizing a binding domain from protein A. *Proc. Natl. Acad. Sci. USA*. 93, 5688-5692.
Gu, H., et al. (1995). A phage display system for studying the sequence determinants of protein folding. *Protein Science*. 4, 1108-1117.
Hubbard, S.J., F. Eisenmenger, and J.M. Thornton. (1994). Modeling studies of the change in conformation required for cleavage of limited proteolytic sites. *Protein Science*. 3, 757-768.
Fontana, A., et al. (1997). Probing the partly folded states of proteins by limited proteolysis. *Folding & Design*. 2, R17-R26.
Kamtekar, S., et al. (1993). Protein Design by Binary Patterning of Polar and Nonpolar Amino Acids. *Science*. 262, 1680-1685.
Davidson, A.R. and R.T. Sauer. (1994). Folded proteins occur frequently in libraries of random amino acid sequences. *Proc. Natl. Acad. Sci. USA*. 91, 2146-2150.
Davidson, A.R., K.J. Lumb, and R.T. Sauer. (1995). Cooperatively folded proteins in random sequence libraries. *Nature Structural Biology*. 2(10), 856-864.
Matthews, D.J. and J.A. Wells. (1993). Substrate Phage: Selection of Protease Substrates by Monovalent Phage Display. *Science*. 260, 1113-1117.
Riechmann, L. and P. Holliger. (1997). The C-Terminal Domain of TolA Is the Coreceptor for Filamentous Phage Infection of *E. coli*. *Cell*. 90, 351-360.
Smith, G.P. (1985). Filamentous Fusion Phage: Novel Expression Vectors That Display Cloned Antigens on the Virion Surface. *Science*. 228, 1315-1317.
Krebber, C., et al. (1997). Selectively-infective Phage (SIP): A Mechanistic Dissection of a Novel in vivo Selection for Protein-ligand Interactions. *Journal of Molecular Biology*. 268, 607-618.
Stengele, I., et al. (1990). Dissection of Functional Domains in Phage fd Adsorption Protein. Discrimination between Attachment and Penetration. *Journal of Molecular Biology*. 212, 143-149.
Gray, C.W., R.S. Brown, and D.A. Marvin. (1981). Adsorption complex of Filamentous fd virus. *Journal of Molecular Biology*. 146, 621-627.
Hoogenboom, H.R., et al. (1991). Multi-subunit proteins on the surface of filamentous phage: methodologies for displaying antibody (Fab) heavy and light chains. *Nucleic Acids Research*. 19, 4133-4137.
Bass, S., R. Greene, and J.A. Wells. (1990). Hormone Phage: An Enrichment Method for Variant Proteins With Altered Binding Properties. *Proteins*. 8, 309-314.
Nissim, A., et al. (1994). Antibody fragments from a "single pot" phage display library as immunochemical reagents. *The EMBO Journal*. 13, 692-698.
Marzari, R., et al. (1997). Extending filamentous phage host range by the grafting of a heterologous receptor binding domain. *Gene*. 185, 27-33.

Mossakowska, D.E., K. Nyberg, and A.R. Fersht. (1989). Kinetic Characterisation of the Recombinant Ribonuclease from *Bacillus amyloliquefaciens* (Barnase) and Investigation of Key Residues in Catalysis by Site-Directed Mutagenesis. *Biochemistry*. 28, 3843-3850.
Meiering, E.M., L. Serrano, and A.R. Fersht. (1992). Effect of Active Site Residues in Barnase on Activity and Stability. *Journal of Molecular Biology*. 225, 585-589.
Serrano, L., et al. (1992). The Folding of an Enzyme. II Substructure of Barnase and the Contribution of Different Interactions to Protein Stability. *Journal of Molecular Biology*. 224, 783-804.
McKnight, C.J., P.T. Matsudaira, and P.S. Kim. (1997). NMR structure of the 35-residue villin headpiece subdomain. *Nature Structural Biology*. 4(3), 180-184.
McKnight, C.J., et al. (1996). A Thermostable 35-Residue Subdomain within Villin Headpiece. *Journal of Molecular Biology*. 260, 126-134.
Xu, D. and R. Nussinov. (1997). Favorable domain size in proteins. *Folding & Design*. 3, 11-17.
Kippen, A.D. and A.R. Fersht. (1995). Analysis of the Mechanism of Assembly of Cleaved Barnase from Two Peptide Fragments and Its Relevance to the Folding Pathway of Uncleaved Barnase. *Biochemistry*. 34, 1464-1468.
Gay, G.d.P. and A.R. Fersht. (1994). Generation of a Family of Protein Fragments for Structure-Folding Studies. 1. Folding Complementation of Two Fragments of Chymotrypsin Inhibitor-2 Formed by Cleavage at Its Unique Methionine Residue. *Biochemistry*. 33, 7957-7963.
Wu, L.C., R. Grandori, and J. Carey. (1994). Autonomous subdomains in protein folding. *Protein Science*. 3, 369-371.
Kwon, W.S., N.A.D. Silva, and J.T. Kellis. (1996). Relationships between thermal stability, degradation rate and expression yield of barnase variants in the periplasm of *Escherichia coli*. *Protein Engineering*. 9(12), 1197-1202.
Axe, D.D., N.W. Foster, and A.R. Fersht. (1996). Active barnase variants with completely random hydrophobic cores. *Proc. Natl. Acad. Sci. USA*. 93, 5590-5594.
Waldburger, C.D., J.F. Schildbach, and R.T. Sauer. (1995). Are buried salt bridges important for protein stability and conformational specificity? *Nature Structural Biology*. 2(2), 122-128.
Roy, S., et al. (1997). A Protein Designed by Binary Patterning of Polar and Nonpolar Amino Acids Displays Native-like Properties. *Journal of the American Chemical Society*. 119, 5302-5306.
Clackson, T., et al. (1991). Making antibody fragments using phage display libraries. *Nature*. 352, 624-628.
McCafferty, J., et al. (1990). Phage antibodies: filamentous phage displaying antibody variable domains. *Nature*. 348, 552-554.
Fisch, I., et at. (1996). A strategy of exon shuffling for making large peptide repertoires displayed on filamentous bacteriophage. *Proc. Natl. Acad. Sci. USA*. 93, 7761-7766.
Matouschek, A., et al. (1989). Mapping the transition state and pathway of protein folding by protein engineering. *Nature*. 340, 122-126.
Laemmli, U.K. (1970). Cleavage of structural proteins during the assembly of the head of bacteriophage T4. *Nature*. 227, 680-685.
Schatz, G. and Dobberstein, B. (1996). Common principles of protein translocation across membranes. *Science*. 271, 1519-1526.
Von Heijne, G. (1998). Life and death of a signal peptide. *Nature*. 396, 111-113.
Sprengart, M.L., Fuchs, E. and Porter, A.G. (1996). The downstream box: an efficient and independent translation initiation signal in *E.coli*. *The EMBO Journal*. 15, 665-674.
Perlman, D. and Halvorson, H.O. (1983). A putative signal peptidase recognition site and sequence in eukaryotic and prokaryotic signal peptides. *Journal of Molecular Biology*. 167, 391-409.
Von Heijne, G. (1983). Patterns of amino acids near signal-sequence cleavage sites. *Eur. J. Biochem*. 133, 17-21.
Pedersen, H., Hölder, S., Sutherlin, D.P., Schwitter, U., King, D.S., Schultz, P.G. (1998). *Proc. Natl. Acad. Sci. USA*. 95, 10523-10528.
Kristensen et al., "Proteolytic selection for protein folding using filamentous bacteriophage," *Folding & Design* (1998) 3:321-328.

(56) References Cited

OTHER PUBLICATIONS

Sieber et al., "Selecting proteins with improved stability by a phage-based method," Nature Biotechnology (1998) 16:955-960.

Clackson et al., "In vitro selection from protein and peptide libraries," TIBTECH (1994) 12:173-184.

McConnell et al., "Construction and screening of M13 phage libraries displaying long random peptides," Molecular Diversity, 1 (1995) 165-176.

Ward et al., "Retrieval of human antibodies from phage-display libraries using enzymatic cleavage," J. of Immunological Methods 189 (1996), 73-82.

* cited by examiner

SEQUENCE LISTING

```
<160> NUMBER OF SEQ ID NOS: 80

<210> SEQ ID NO 1
<211> LENGTH: 17
<212> TYPE: PRT
<213> ORGANISM: Artificial Sequence
<220> FEATURE:
<223> OTHER INFORMATION: Synthetic linker peptide sequence with protease
      recognition sites
<220> FEATURE:
<221> NAME/KEY: MISC_FEATURE
<222> LOCATION: (1)..(17)
<223> OTHER INFORMATION: Synthetic linker peptide sequence with protease
      recognition sites

<400> SEQUENCE: 1

Pro Ala Gly Leu Ser Glu Gly Ser Thr Ile Glu Gly Arg Gly Ala His
1               5                   10                  15

Glu
```

```
<210> SEQ ID NO 2
<211> LENGTH: 57
<212> TYPE: DNA
<213> ORGANISM: Artificial Sequence
<220> FEATURE:
<223> OTHER INFORMATION: Synthetic PCR primer for vector
      construction/screening.
<220> FEATURE:
<221> NAME/KEY: misc_feature
<222> LOCATION: (1)..(57)
<223> OTHER INFORMATION: Synthetic PCR primer for vector
      construction/screening

<400> SEQUENCE: 2
ggcaccctca gaacggtacc ccaccctcag aggccggctg ggccgccacc ctcagag        57

<210> SEQ ID NO 3
<211> LENGTH: 89
<212> TYPE: DNA
<213> ORGANISM: Artificial sequence
<220> FEATURE:
<223> OTHER INFORMATION: Synthetic PCR primer for vector
      construction/screening.
<220> FEATURE:
<221> NAME/KEY: misc_feature
<222> LOCATION: (1)..(89)
<223> OTHER INFORMATION: Synthetic PCR primer for vector
      construction/screening

<400> SEQUENCE: 3
ggtggcggcc cagccggcct ttctgagggg tcgactatag aaggacgagg gcccagcgaa     60
ggaggtgggg tacccccttc tgagggtgg                                       89

<210> SEQ ID NO 4
<211> LENGTH: 89
<212> TYPE: DNA
<213> ORGANISM: Artificial sequence
<220> FEATURE:
<223> OTHER INFORMATION: Synthetic PCR primer for vector
      construction/screening.
<220> FEATURE:
<221> NAME/KEY: misc_feature
<222> LOCATION: (1)..(89)
<223> OTHER INFORMATION: Synthetic PCR primer for vector
      construction/screening

<400> SEQUENCE: 4
ccaccctcag aaggggtac cccacctcct tcgctgggcc ctcgtccttc tatagtcgac      60
ccctcagaaa ggccggctgg gccgccacc                                       89

<210> SEQ ID NO 5
<211> LENGTH: 24
<212> TYPE: DNA
<213> ORGANISM: Artificial sequence
<220> FEATURE:
<223> OTHER INFORMATION: Synthetic PCR primer for vector
      construction/screening.
<220> FEATURE:
<221> NAME/KEY: misc_feature
<222> LOCATION: (1)..(24)
<223> OTHER INFORMATION: Synthetic PCR primer for vector
      construction/screening

<400> SEQUENCE: 5
gcgatggttg ttgtcattgt cggc                                            24

<210> SEQ ID NO 6
<211> LENGTH: 24
<212> TYPE: DNA
```

```
<213> ORGANISM: Artificial sequence
<220> FEATURE:
<223> OTHER INFORMATION: Synthetic PCR primer for vector
      construction/screening.
<220> FEATURE:
<221> NAME/KEY: misc_feature
<222> LOCATION: (1)..(24)
<223> OTHER INFORMATION: Synthetic PCR primer for vector
      construction/screening

<400> SEQUENCE: 6
aaaagaaacg caaagacacc acgg                                           24

<210> SEQ ID NO 7
<211> LENGTH: 23
<212> TYPE: DNA
<213> ORGANISM: Artificial sequence
<220> FEATURE:
<223> OTHER INFORMATION: Synthetic PCR primer for vector
      construction/screening.
<220> FEATURE:
<221> NAME/KEY: misc_feature
<222> LOCATION: (1)..(23)
<223> OTHER INFORMATION: Synthetic PCR primer for vector
      construction/screening

<400> SEQUENCE: 7
cctcctgagt acggtgatac acc                                            23

<210> SEQ ID NO 8
<211> LENGTH: 24
<212> TYPE: DNA
<213> ORGANISM: Artificial sequence
<220> FEATURE:
<223> OTHER INFORMATION: Synthetic PCR primer used to screen for
      recombinant clones.
<220> FEATURE:
<221> NAME/KEY: misc_feature
<222> LOCATION: (1)..(24)
<223> OTHER INFORMATION: Synthetic PCR primer used to screen for
      recombinant clones

<400> SEQUENCE: 8
gtaaattcag agactgcgct ttcc                                           24

<210> SEQ ID NO 9
<211> LENGTH: 26
<212> TYPE: DNA
<213> ORGANISM: Artificial sequence
<220> FEATURE:
<223> OTHER INFORMATION: Synthetic PCR primer used to screen for
      recombinant clones.
<220> FEATURE:
<221> NAME/KEY: misc_feature
<222> LOCATION: (1)..(26)
<223> OTHER INFORMATION: Synthetic PCR primer used to screen for
      recombinant clones

<400> SEQUENCE: 9
attttcggtc atagcccct tattag                                          26

<210> SEQ ID NO 10
<211> LENGTH: 65
<212> TYPE: DNA
<213> ORGANISM: Artificial sequence
<220> FEATURE:
<223> OTHER INFORMATION: Synthetic PCR primer recognizing FLAG tag
      nucleotide sequence.
<220> FEATURE:
<221> NAME/KEY: misc_feature
<222> LOCATION: (1)..(65)
<223> OTHER INFORMATION: Synthetic PCR primer recognizing FLAG tag
``` nucleotide sequence

<400> SEQUENCE: 10
caaacgggcg gccgcagact acaaggatga cgacgacaag gaaactgttg aaagttgttt    60
agcaa                                                                65

<210> SEQ ID NO 11
<211> LENGTH: 51
<212> TYPE: DNA
<213> ORGANISM: Artificial sequence
<220> FEATURE:
<223> OTHER INFORMATION: Synthetic PCR primer used to change codon
      usage in recombinant cl ones.
<220> FEATURE:
<221> NAME/KEY: misc_feature
<222> LOCATION: (1)..(51)
<223> OTHER INFORMATION: Synthetic PCR primer used to change codon
      usage in recombinant cl ones

<400> SEQUENCE: 11
cccctcagaa aggccggctg ggccgccgcc agcattgaca ggaggttcag g              51

<210> SEQ ID NO 12
<211> LENGTH: 52
<212> TYPE: DNA
<213> ORGANISM: Artificial sequence
<220> FEATURE:
<223> OTHER INFORMATION: Synthetic PCR primer used to change codon
      usage in recombinant cl ones.
<220> FEATURE:
<221> NAME/KEY: misc_feature
<222> LOCATION: (1)..(52)
<223> OTHER INFORMATION: Synthetic PCR primer used to change codon
      usage in recombinant cl ones

<400> SEQUENCE: 12
gaaggaggtg gggtacccgg ttccgagggt ggttccggtt ccggtgattt tg            52

<210> SEQ ID NO 13
<211> LENGTH: 36
<212> TYPE: DNA
<213> ORGANISM: Artificial sequence
<220> FEATURE:
<223> OTHER INFORMATION: Synthetic PCR primer for vector
      construction/screening.
<220> FEATURE:
<221> NAME/KEY: misc_feature
<222> LOCATION: (1)..(36)
<223> OTHER INFORMATION: Synthetic PCR primer for vector
      construction/screening

<400> SEQUENCE: 13
ccctcggaac cggtacccca gctgcttcgt gggccc                              36

<210> SEQ ID NO 14
<211> LENGTH: 47
<212> TYPE: DNA
<213> ORGANISM: Bacillus amyloliquefaciens

<400> SEQUENCE: 14
ctggcggcgg cccagccggc cctgcacagg ttatcaacac gtttgac                  47

<210> SEQ ID NO 15
<211> LENGTH: 43
<212> TYPE: DNA
<213> ORGANISM: Bacillus amyloliquefaciens

<400> SEQUENCE: 15

```
ctcggaaccg tacctctga tttttgtaaa ggtctgataa gcg                    43
```

<210> SEQ ID NO 16
<211> LENGTH: 44
<212> TYPE: DNA
<213> ORGANISM: Gallus gallus

<400> SEQUENCE: 16

```
ggcggcccag ccggccttc tctctctgac gaggacttca aggc                  44
```

<210> SEQ ID NO 17
<211> LENGTH: 41
<212> TYPE: DNA
<213> ORGANISM: Gallus gallus

<400> SEQUENCE: 17

```
cctcggaacc ggtaccgaag agtcctttct ccttcttgag g                    41
```

<210> SEQ ID NO 18
<211> LENGTH: 18
<212> TYPE: DNA
<213> ORGANISM: Artificial sequence
<220> FEATURE:
<223> OTHER INFORMATION: Synthetic PCR primer used for library
      construction.
<220> FEATURE:
<221> NAME/KEY: misc_feature
<222> LOCATION: (1)..(18)
<223> OTHER INFORMATION: Synthetic PCR primer used for library
      construction

<400> SEQUENCE: 18

```
tacgccaagc ttgcatgc                                              18
```

<210> SEQ ID NO 19
<211> LENGTH: 17
<212> TYPE: DNA
<213> ORGANISM: Artificial sequence
<220> FEATURE:
<223> OTHER INFORMATION: Synthetic PCR primer used for library
      construction.
<220> FEATURE:
<221> NAME/KEY: misc_feature
<222> LOCATION: (1)..(17)
<223> OTHER INFORMATION: Synthetic PCR primer used for library
      constuction

<400> SEQUENCE: 19

```
ctgcacctgg gccatgg                                               17
```

<210> SEQ ID NO 20
<211> LENGTH: 17
<212> TYPE: DNA
<213> ORGANISM: Artificial sequence
<220> FEATURE:
<223> OTHER INFORMATION: Synthetic PCR primer used for library
      construction.
<220> FEATURE:
<221> NAME/KEY: misc_feature
<222> LOCATION: (1)..(17)
<223> OTHER INFORMATION: Synthetic PCR primer used for library
      construction

<400> SEQUENCE: 20

```
gattacgcca agctttg                                               17
```

<210> SEQ ID NO 21
<211> LENGTH: 126
<212> TYPE: DNA

```
<213> ORGANISM: Erwinia chrysanthemi
<220> FEATURE:
<221> NAME/KEY: misc_feature
<223> OTHER INFORMATION: n at positions 23, 24, 29, 55, 56, 81, 97,
      101, and 102 can be G, A, T or C
<220> FEATURE:
<221> NAME/KEY: misc_feature
<222> LOCATION: (23)..(23)
<223> OTHER INFORMATION: n at position 23 can be G, A, T or C
<220> FEATURE:
<221> NAME/KEY: misc_feature
<222> LOCATION: (24)..(24)
<223> OTHER INFORMATION: n at position 24 can be G, A, T or C
<220> FEATURE:
<221> NAME/KEY: misc_feature
<222> LOCATION: (29)..(29)
<223> OTHER INFORMATION: n at position 29 can be G, A, T or C
<220> FEATURE:
<221> NAME/KEY: misc_feature
<222> LOCATION: (55)..(55)
<223> OTHER INFORMATION: n at position 55 can be G, A, T or C
<220> FEATURE:
<221> NAME/KEY: misc_feature
<222> LOCATION: (56)..(56)
<223> OTHER INFORMATION: n at position 56 can be G, A, T or C
<220> FEATURE:
<221> NAME/KEY: misc_feature
<222> LOCATION: (81)..(81)
<223> OTHER INFORMATION: n at position 81 can be G, A, T or C
<220> FEATURE:
<221> NAME/KEY: misc_feature
<222> LOCATION: (97)..(97)
<223> OTHER INFORMATION: n at position 97 can be G, A, T or C
<220> FEATURE:
<221> NAME/KEY: misc_feature
<222> LOCATION: (101)..(101)
<223> OTHER INFORMATION: n at position 101 can be G, A, T or C
<220> FEATURE:
<221> NAME/KEY: misc_feature
<222> LOCATION: (102)..(102)
<223> OTHER INFORMATION: n at position 102 can be G, A, T or C

<400> SEQUENCE: 21
gattacgcca agcttgcatg cannddctnt dtcaaggaga cagtcataat garrnnbcta      60
ttgsyaayrs yasyasyagb nttgttatta ctcsyanycv nncygdccat ggcccaggtg     120
cagctg                                                               126

<210> SEQ ID NO 22
<211> LENGTH: 117
<212> TYPE: DNA
<213> ORGANISM: Bacteriophage M13mp18
<220> FEATURE:
<221> NAME/KEY: misc_feature
<222> LOCATION: (18)..(18)
<223> OTHER INFORMATION: Nucleotide at position 18 can be G, A, T or C.
<220> FEATURE:
<221> NAME/KEY: misc_feature
<222> LOCATION: (19)..(19)
<223> OTHER INFORMATION: Nucleotide at position 19 can be G, A, T or C.
<220> FEATURE:
<221> NAME/KEY: misc_feature
<222> LOCATION: (20)..(20)
<223> OTHER INFORMATION: Nucleotide at position 20 can be G, A, T or C.
<220> FEATURE:
<221> NAME/KEY: misc_feature
<222> LOCATION: (21)..(21)
<223> OTHER INFORMATION: Nucleotide at position 21 can be G, A, T or C.

<400> SEQUENCE: 22
gattacgcca agctttgnnn nctttttttww ggagattttc aacrtgaraa rattattatt      60
csyaattsyt ttagttsyts ytttctwtgy ggyccagccg gccatggccc aggtgca         117

<210> SEQ ID NO 23
```

```
<211> LENGTH: 18
<212> TYPE: DNA
<213> ORGANISM: Artificial sequence
<220> FEATURE:
<223> OTHER INFORMATION: Synthetic PCR primer used for vector
      construction.

<400> SEQUENCE: 23
ctttatgctt ccggctcg                                              18

<210> SEQ ID NO 24
<211> LENGTH: 17
<212> TYPE: DNA
<213> ORGANISM: Artificial sequence
<220> FEATURE:
<223> OTHER INFORMATION: Synthetic PCR primer for library construction.
<220> FEATURE:
<221> NAME/KEY: misc_feature
<222> LOCATION: (1)..(17)
<223> OTHER INFORMATION: Synthetic PCR primer for library construction

<400> SEQUENCE: 24 cggcccatt cagatcc                                                17

<210> SEQ ID NO 25
<211> LENGTH: 50
<212> TYPE: DNA
<213> ORGANISM: Artificial sequence
<220> FEATURE:
<223> OTHER INFORMATION: Randomized E. chrysanthemi pelB sequence.
<220> FEATURE:
<221> NAME/KEY: misc_feature
<222> LOCATION: (1)..(50)
<223> OTHER INFORMATION: Randomized E. chrysanthemi pelB sequence

<400> SEQUENCE: 25
aagcttgcat gcaaattcta tdtcaaggag acagttataa tgaaatacct           50

<210> SEQ ID NO 26
<211> LENGTH: 50
<212> TYPE: DNA
<213> ORGANISM: Artificial sequence
<220> FEATURE:
<223> OTHER INFORMATION: Randomized E. chrysanthemi pelB sequence.
<220> FEATURE:
<221> NAME/KEY: misc_feature
<222> LOCATION: (1)..(50)
<223> OTHER INFORMATION: Randomized E. chrysanthemi pelB sequence
<220> FEATURE:
<221> NAME/KEY: misc_feature
<222> LOCATION: (14)..(14)
<223> OTHER INFORMATION: n at position 14 can be G, A, T or C.
<220> FEATURE:
<221> NAME/KEY: misc_feature
<222> LOCATION: (15)..(15)
<223> OTHER INFORMATION: n at position 15 can be G, A, T or C.
<220> FEATURE:
<221> NAME/KEY: misc_feature
<222> LOCATION: (20)..(20)
<223> OTHER INFORMATION: n at position 20 can be G, A, T or C.
<220> FEATURE:
<221> NAME/KEY: misc_feature
<222> LOCATION: (45)..(45)
<223> OTHER INFORMATION: n at position 45 can be G, A, T or C.
<220> FEATURE:
<221> NAME/KEY: misc_feature
<222> LOCATION: (46)..(46)
<223> OTHER INFORMATION: n at position 46 can be G, A, T or C.

<400> SEQUENCE: 26
aagcttgcat gcannddctn tdtcaaggag acagtcataa tgarrnnbct           50
```

```
<210> SEQ ID NO 27
<211> LENGTH: 50
<212> TYPE: DNA
<213> ORGANISM: Artificial sequence
<220> FEATURE:
<223> OTHER INFORMATION: Randomized E. chrysanthemi pelB sequence.
<220> FEATURE:
<221> NAME/KEY: misc_feature
<222> LOCATION: (1)..(50)
<223> OTHER INFORMATION: Randomized E. chrysanthemi pelB sequence

<400> SEQUENCE: 27
aagcttgcat gcagcatctc tdgcaaggag acagtcataa tgaagacgct              50

<210> SEQ ID NO 28
<211> LENGTH: 50
<212> TYPE: DNA
<213> ORGANISM: Artificial sequence
<220> FEATURE:
<223> OTHER INFORMATION: Randomized E. chrysanthemi pelB sequence.
<220> FEATURE:
<221> NAME/KEY: misc_feature
<222> LOCATION: (1)..(50)
<223> OTHER INFORMATION: Randomized E. chrysanthemi pelB sequence

<400> SEQUENCE: 28
aagcttgcat gcacgggctg tdtcaaggag acagtcataa tgagagggct              50

<210> SEQ ID NO 29
<211> LENGTH: 50
<212> TYPE: DNA
<213> ORGANISM: Artificial sequence
<220> FEATURE:
<223> OTHER INFORMATION: Randomized E. chrysanthemi pelB sequence.
<220> FEATURE:
<221> NAME/KEY: misc_feature
<222> LOCATION: (1)..(50)
<223> OTHER INFORMATION: Randomized E. chrysanthemi pelB sequence

<400> SEQUENCE: 29
aagcttgcat gcaccagctc tdtcaaggag acagtcataa tgaggcggct              50

<210> SEQ ID NO 30
<211> LENGTH: 55
<212> TYPE: DNA
<213> ORGANISM: Artificial sequence
<220> FEATURE:
<223> OTHER INFORMATION: Randomized E. chrysanthemi pelB sequence.
<220> FEATURE:
<221> NAME/KEY: misc_feature
<222> LOCATION: (1)..(55)
<223> OTHER INFORMATION: Randomized E. chrysanthemi pelB sequence

<400> SEQUENCE: 30
attcctaacg gcagccgctg gattgttatt actcgcggcc cagccggcca tggcc        55

<210> SEQ ID NO 31
<211> LENGTH: 55
<212> TYPE: DNA
<213> ORGANISM: Artificial sequence
<220> FEATURE:
<223> OTHER INFORMATION: Randomized E. chrysanthemi pelB sequence.
<220> FEATURE:
<221> NAME/KEY: misc_feature
<222> LOCATION: (1)..(55)
<223> OTHER INFORMATION: Randomized E. chrysanthemi pelB sequence
<220> FEATURE:
<221> NAME/KEY: misc_feature
<222> LOCATION: (22)..(22)
<223> OTHER INFORMATION: n at position 22 can be G, A, T or C.
<220> FEATURE:
<221> NAME/KEY: misc_feature
```

<222> LOCATION: (38)..(38)
<223> OTHER INFORMATION: n at position 38 can be G, A, T or C.
<220> FEATURE:
<221> NAME/KEY: misc_feature
<222> LOCATION: (42)..(42)
<223> OTHER INFORMATION: n at position 42 can be G, A, T or C.
<220> FEATURE:
<221> NAME/KEY: misc_feature
<222> LOCATION: (43)..(43)
<223> OTHER INFORMATION: n at position 43 can be G, A, T or C.

<400> SEQUENCE: 31
attgsyaayr syasyasyag bnttgttatt actcsyanyc vnncygdcca tggcc    55

<210> SEQ ID NO 32
<211> LENGTH: 55
<212> TYPE: DNA
<213> ORGANISM: Artificial sequence
<220> FEATURE:
<223> OTHER INFORMATION: Randomized E. chrysanthemi pelB sequence.
<220> FEATURE:
<221> NAME/KEY: misc_feature
<222> LOCATION: (1)..(55)
<223> OTHER INFORMATION: Randomized E. chrysanthemi pelB sequence

<400> SEQUENCE: 32
attgcyaatg gtactgtyag gattgttatt actcccaccc ggtccgtcca tggcc    55

<210> SEQ ID NO 33
<211> LENGTH: 55
<212> TYPE: DNA
<213> ORGANISM: Artificial sequence
<220> FEATURE:
<223> OTHER INFORMATION: Randomized E. chrysanthemi pelB sequence.
<220> FEATURE:
<221> NAME/KEY: misc_feature
<222> LOCATION: (1)..(55)
<223> OTHER INFORMATION: Randomized E. chrysanthemi pelB sequence

<400> SEQUENCE: 33
attgcyaatg ctagtgcyag ggttgttatt actcccaatc gcgccggcca tggcc    55

<210> SEQ ID NO 34
<211> LENGTH: 54
<212> TYPE: DNA
<213> ORGANISM: Artificial sequence
<220> FEATURE:
<223> OTHER INFORMATION: Randomized E. chrysanthemi pelB sequence.
<220> FEATURE:
<221> NAME/KEY: misc_feature
<222> LOCATION: (1)..(54)
<223> OTHER INFORMATION: Randomized E. chrysanthemi pelB sequence
<220> FEATURE:
<221> NAME/KEY: misc_feature
<222> LOCATION: (22)..(22)
<223> OTHER INFORMATION: n at position 22 can be G, A, T or C.
<220> FEATURE:
<221> NAME/KEY: misc_feature
<222> LOCATION: (43)..(43)
<223> OTHER INFORMATION: n at position 43 can be G, A, T or C.
<220> FEATURE:
<221> NAME/KEY: misc_feature
<222> LOCATION: (44)..(44)
<223> OTHER INFORMATION: n at position 44 can be G, A, T or C.

<400> SEQUENCE: 34
attggtaata gcagcagtag bnttgttagg actcgcaccc ccnncyadcc atgg 54

<210> SEQ ID NO 35
<211> LENGTH: 22
<212> TYPE: PRT
<213> ORGANISM: Erwinia chrysanthemi -continued

```
<400> SEQUENCE: 35

Met Lys Tyr Leu Leu Pro Thr Ala Ala Ala Gly Leu Leu Leu Leu Ala
1               5                   10                  15
Ala Gln Pro Ala Met Ala
            20

<210> SEQ ID NO 36
<211> LENGTH: 22
<212> TYPE: PRT
<213> ORGANISM: Artificial sequence
<220> FEATURE:
<223> OTHER INFORMATION: Randomized E. chrysanthemi pelB sequence.
<220> FEATURE:
<221> NAME/KEY: MISC_FEATURE
<222> LOCATION: (1)..(22)
<223> OTHER INFORMATION: Randomized E. chrysanthemi pelB sequence

<400> SEQUENCE: 36

Met Lys Thr Leu Ala Met Val Leu Val Gly Gly Pro Pro Gly Pro Ser
1               5                   10                  15
Ala Gln Pro Ala Met Ala
            20

<210> SEQ ID NO 37
<211> LENGTH: 21
<212> TYPE: PRT
<213> ORGANISM: Artificial sequence
<220> FEATURE:
<223> OTHER INFORMATION: Randomized E. chrysanthemi pelB sequence.
<220> FEATURE:
<221> NAME/KEY: MISC_FEATURE
<222> LOCATION: (1)..(21)
<223> OTHER INFORMATION: Randomized E. chrysanthemi pelB sequence

<400> SEQUENCE: 37

Met Arg Gly Leu Ala Met Leu Val Ala Gly Gly Pro Ile Ala Pro Ala
1               5                   10                  15
Gln Pro Ala Met Ala
            20

<210> SEQ ID NO 38
<211> LENGTH: 23
<212> TYPE: PRT
<213> ORGANISM: Artificial sequence
<220> FEATURE:
<223> OTHER INFORMATION: Randomized E. chrysanthemi pelB sequence.
<220> FEATURE:
<221> NAME/KEY: MISC_FEATURE
<222> LOCATION: (1)..(23)
<223> OTHER INFORMATION: Randomized E. chrysanthemi pelB sequence

<400> SEQUENCE: 38

Met Arg Arg Leu Val Pro Ile Thr Ala Ala Val Gly Leu Leu Ala Pro
1               5                   10                  15
Pro Thr Gln Pro Ala Met Ala
            20

<210> SEQ ID NO 39
<211> LENGTH: 50
<212> TYPE: DNA
<213> ORGANISM: Artificial sequence
<220> FEATURE:
<223> OTHER INFORMATION: Randomized bacteriophage M13 g3 sequence.
<220> FEATURE:
<221> NAME/KEY: misc_feature
<222> LOCATION: (1)..(50)
<223> OTHER INFORMATION: Randomized bacteriophage M13 g3 sequence
```

<400> SEQUENCE: 39
aagctttgga cgcttttttt tggagatttt caacgtgaaa aaattattat         50

<210> SEQ ID NO 40
<211> LENGTH: 50
<212> TYPE: DNA
<213> ORGANISM: Artificial sequence
<220> FEATURE:
<223> OTHER INFORMATION: Randomized bacteriophage M13 g3 sequence.
<220> FEATURE:
<221> NAME/KEY: misc_feature
<222> LOCATION: (9)..(9)
<223> OTHER INFORMATION: n at position 9 is can be G, A, t or C.
<220> FEATURE:
<221> NAME/KEY: misc_feature
<222> LOCATION: (1)..(50)
<223> OTHER INFORMATION: Randomized bacteriophage M13 g3 sequence
<220> FEATURE:
<221> NAME/KEY: misc_feature
<222> LOCATION: (10)..(10)
<223> OTHER INFORMATION: n at position 10 is can be G, A, t or C.
<220> FEATURE:
<221> NAME/KEY: misc_feature
<222> LOCATION: (11)..(11)
<223> OTHER INFORMATION: n at position 11 is can be G, A, t or C.
<220> FEATURE:
<221> NAME/KEY: misc_feature
<222> LOCATION: (12)..(12)
<223> OTHER INFORMATION: n at position 12 is can be G, A, t or C.

<400> SEQUENCE: 40
aagctttgnn nnctttttw wggagatttt caacrtgara arattattat         50

<210> SEQ ID NO 41
<211> LENGTH: 50
<212> TYPE: DNA
<213> ORGANISM: Artificial sequence
<220> FEATURE:
<223> OTHER INFORMATION: Randomized bacteriophage M13 g3 sequence.
<220> FEATURE:
<221> NAME/KEY: misc_feature
<222> LOCATION: (1)..(50)
<223> OTHER INFORMATION: Randomized bacteriophage M13 g3 sequence.

<400> SEQUENCE: 41
aagctttggg gccttttttt aggagatttt caacatgaga agattattat         50

<210> SEQ ID NO 42
<211> LENGTH: 50
<212> TYPE: DNA
<213> ORGANISM: Artificial sequence
<220> FEATURE:
<223> OTHER INFORMATION: Randomized bacteriophage M13 g3 sequence.
<220> FEATURE:
<221> NAME/KEY: misc_feature
<222> LOCATION: (1)..(50)
<223> OTHER INFORMATION: Randomized bacteriophage M13 g3 sequence

<400> SEQUENCE: 42
tcgcaattcc tttagttgtt cctttctatg cggcccagcc ggccatggcc         50

<210> SEQ ID NO 43
<211> LENGTH: 50
<212> TYPE: DNA
<213> ORGANISM: Artificial sequence
<220> FEATURE:
<223> OTHER INFORMATION: Randomized bacteriophage M13 g3 sequence.
<220> FEATURE:
<221> NAME/KEY: misc_feature
<222> LOCATION: (1)..(50)
<223> OTHER INFORMATION: Randomized bacteriophage M13 g3 sequence -continued

```
<400> SEQUENCE: 43
tcsyaattsy tttagttsyt sytttctwtg yggyccagcc ggccatggcc                 50

<210> SEQ ID NO 44
<211> LENGTH: 50
<212> TYPE: DNA
<213> ORGANISM: Artificial sequence
<220> FEATURE:
<223> OTHER INFORMATION: Randomized bacteriophage M13 g3 sequence.
<220> FEATURE:
<221> NAME/KEY: misc_feature
<222> LOCATION: (1)..(50)
<223> OTHER INFORMATION: Randomized bacteriophage M13 g3 sequence

<400> SEQUENCE: 44
tcctaattcc tttagttgtt gctttctatg tggtccagcc ggccatggcc                 50

<210> SEQ ID NO 45
<211> LENGTH: 22
<212> TYPE: PRT
<213> ORGANISM: Artificial sequence
<220> FEATURE:
<223> OTHER INFORMATION: Randomized bacteriophage M13 g3 sequence.
<220> FEATURE:
<221> NAME/KEY: MISC_FEATURE
<222> LOCATION: (1)..(22)
<223> OTHER INFORMATION: Randomized bacteriophage M13 g3 sequence

<400> SEQUENCE: 45

Met Lys Lys Leu Leu Phe Ala Ile Pro Leu Val Val Pro Phe Tyr Ala
1               5                   10                  15

Ala Gln Pro Ala Met Ala
            20

<210> SEQ ID NO 46
<211> LENGTH: 22
<212> TYPE: PRT
<213> ORGANISM: Artificial sequence
<220> FEATURE:
<223> OTHER INFORMATION: Randomized bacteriophage M13 g3 sequence.
<220> FEATURE:
<221> NAME/KEY: MISC_FEATURE
<222> LOCATION: (1)..(22)
<223> OTHER INFORMATION: Randomized bacteriophage M13 g3 sequence

<400> SEQUENCE: 46

Met Arg Arg Leu Leu Leu Ala Pro Pro Val Ala Val Pro Phe Tyr Val
1               5                   10                  15

Val Gln Pro Ala Met Ala
            20

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide primer used as a
      substrate for Stoffel fragment of Thermus aquaticus DNA
      polymerase I.
<220> FEATURE:
<221> NAME/KEY: misc_feature
<222> LOCATION: (1)..(18)
<223> OTHER INFORMATION: Synthetic oligonucleotide primer used as
      substrate for Stoffel fragment of Thermus aquaticus DNA
      polymerase I

<400> SEQUENCE: 47
tttcgcaaga tgtggcgt                                                   18
```

```
<210> SEQ ID NO 48
<211> LENGTH: 12
<212> TYPE: DNA
<213> ORGANISM: Artificial sequence
<220> FEATURE:
<223> OTHER INFORMATION: Synthetic oligonucleotide primer used as a
      substrate for Thermus aquaticus DNA polymerase I.
<220> FEATURE:
<221> NAME/KEY: misc_feature
<222> LOCATION: (1)..(12)
<223> OTHER INFORMATION: Synthetic primer used as substrate for Stoffel
      fragment of Thermus aquaticus DNA polymerase I

<400> SEQUENCE: 48
gcgaagatgt gg                                                           12

<210> SEQ ID NO 49
<211> LENGTH: 30
<212> TYPE: DNA
<213> ORGANISM: Artificial sequence
<220> FEATURE:
<223> OTHER INFORMATION: Synthetic oligonucleotide primer used as a
      substrate for Thermus aquaticus DNA polymerase I.
<220> FEATURE:
<221> NAME/KEY: misc_feature
<222> LOCATION: (1)..(30)
<223> OTHER INFORMATION: Synthetic oligonucleotide primer used as
      substrate for Thermus aquaticus DNA polymerase I

<400> SEQUENCE: 49
aaatacaaca ataaaacgcc acatcttgcg                                        30

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide sequence insert
      containing PstI restriction site and frame shift for H102A mutant
      barnase fusion construct fused to p3 gene of phage fd-3.
<220> FEATURE:
<221> NAME/KEY: misc_feature
<222> LOCATION: (1)..(20)
<223> OTHER INFORMATION: Synthetic oligonucleotide sequence insert
      containing PstI restriction site and frame shift for H102A mutant
      barnase fusion construct fused to p3 gene of phage fd-3.

<400> SEQUENCE: 50
ctgcaggcgg tgcggccgca                                                   20

<210> SEQ ID NO 51
<211> LENGTH: 24
<212> TYPE: DNA
<213> ORGANISM: Artificial sequence
<220> FEATURE:
<223> OTHER INFORMATION: Synthetic oligonucleotide used for random
      priming.
<220> FEATURE:
<221> NAME/KEY: misc_feature
<222> LOCATION: (1)..(24)
<223> OTHER INFORMATION: Synthetic oligonucleotide used for random
      priming
<220> FEATURE:
<221> NAME/KEY: misc_feature
<222> LOCATION: (19)..(19)
<223> OTHER INFORMATION: n at position 19 can be G, A, T or C.
<220> FEATURE:
<221> NAME/KEY: misc_feature
<222> LOCATION: (20)..(20)
<223> OTHER INFORMATION: n at position 20 can be G, A, T or C.
<220> FEATURE:
<221> NAME/KEY: misc_feature
```

```
<222> LOCATION: (21)..(21)
<223> OTHER INFORMATION: n at position 21 can be G, A, T or C.
<220> FEATURE:
<221> NAME/KEY: misc_feature
<222> LOCATION: (22)..(22)
<223> OTHER INFORMATION: n at position 22 can be G, A, T or C.
<220> FEATURE:
<221> NAME/KEY: misc_feature
<222> LOCATION: (23)..(23)
<223> OTHER INFORMATION: n at position 23 can be G, A, T or C.
<220> FEATURE:
<221> NAME/KEY: misc_feature
<222> LOCATION: (24)..(24)
<223> OTHER INFORMATION: n at position 24 can be G, A, T or C.

<400> SEQUENCE: 51
gagcctgcag agctcaggnn nnnn                                          24

<210> SEQ ID NO 52
<211> LENGTH: 23
<212> TYPE: DNA
<213> ORGANISM: Artificial sequence
<220> FEATURE:
<223> OTHER INFORMATION: Synthetic PCR primer used to re-amplify
      randomply amplified E. coli genomic DNA sequence.
<220> FEATURE:
<221> NAME/KEY: misc_feature
<222> LOCATION: (1)..(23)
<223> OTHER INFORMATION: Synthetic PCR primer used to re-amplify
      randomply amplified E. coli genomic DNA sequences.

<400> SEQUENCE: 52
cgtgcgagcc tgcagagctc agg                                           23

<210> SEQ ID NO 53
<211> LENGTH: 45
<212> TYPE: PRT
<213> ORGANISM: Artificial sequence
<220> FEATURE:
<223> OTHER INFORMATION: Barstar binding barnase-p3 fusion insert.
<220> FEATURE:
<221> NAME/KEY: MISC_FEATURE
<222> LOCATION: (1)..(45)
<223> OTHER INFORMATION: Barstar binding barnase-p3 fusion insert

<400> SEQUENCE: 53

Leu Gln Ser Ser Gly Asp Cys Val Ile Ser Asp Thr Cys Ile Ala Gly
1               5                   10                  15

Met Ala Glu Ala Ala Ala Cys Glu Glu Lys Phe Ser Ser Gln Asn Val
            20                  25                  30

Gly Leu Thr Ile Thr Val Thr Pro Cys Leu Ser Ser Ala
        35                  40                  45

<210> SEQ ID NO 54
<211> LENGTH: 44
<212> TYPE: PRT
<213> ORGANISM: Artificial sequence
<220> FEATURE:
<223> OTHER INFORMATION: Barstar binding barnase-p3 fusion insert.
<220> FEATURE:
<221> NAME/KEY: MISC_FEATURE
<222> LOCATION: (1)..(44)
<223> OTHER INFORMATION: Barstar binding barnase-p3 fusion insert

<400> SEQUENCE: 54

Leu Gln Ser Ser Gly Cys Gly Ser Ser Gly Ser Ser Ile Asn Cys Leu
1               5                   10                  15

Pro Cys Gly Ala Thr Ser Arg Gly Thr Ser Pro Leu Ala Ser Gly Leu
            20                  25                  30
```

```
<210> SEQ ID NO 55
<211> LENGTH: 40
<212> TYPE: PRT
<213> ORGANISM: Artificial sequence
<220> FEATURE:
<223> OTHER INFORMATION: Barstar binding barnase-p3 fusion insert.
<220> FEATURE:
<221> NAME/KEY: MISC_FEATURE
<222> LOCATION: (1)..(40)
<223> OTHER INFORMATION: Barstar binding barnase-p3 fusion insert

<400> SEQUENCE: 55

Leu Gln Ser Ser Gly Asp Ser Ala Gly Cys Lys Asn Met Thr Gly Gly
1               5                   10                  15

Arg Leu Tyr Ala His Thr Leu Glu Ala Ile Ile Pro Gly Phe Ala Val
            20                  25                  30

Ser Ala Pro Ala Cys Glu Pro Ala
        35                  40

<210> SEQ ID NO 56
<211> LENGTH: 33
<212> TYPE: PRT
<213> ORGANISM: Artificial sequence
<220> FEATURE:
<223> OTHER INFORMATION: Barstar binding barnase-p3 fusion insert.
<220> FEATURE:
<221> NAME/KEY: MISC_FEATURE
<222> LOCATION: (1)..(33)
<223> OTHER INFORMATION: Barstar binding barnase-p3 fusion insert

<400> SEQUENCE: 56

Leu Gln Ser Ser Gly Cys Val Arg Leu Lys Arg Thr Ser Val Asn His
1               5                   10                  15

Gln P

```
<222> LOCATION: (1)..(41)
<223> OTHER INFORMATION: Barstar binding barnase-p3 fusion insert

<400

Glu Val Asp Phe Val Asp Thr Pro Gln Glu Val Asp Cys Arg Ala
            35                  40                  45

Ala Leu Ser Ser Ala
    50

<210> SEQ ID NO 62
<211> LENGTH: 33
<212> TYPE: PRT
<213> ORGANISM: Artificial sequence
<220> FEATURE:
<223> OTHER INFORMATION: Barstar binding barnase-p3 fusion insert.
<220> FEATURE:
<221> NAME/KEY: MISC_FEATURE
<222> LOCATION: (1)..(33)
<223> OTHER INFORMATION: Barstar binding barnase-p3 fusion insert

<400> SEQUENCE: 62

Leu Gln Ser Ser Gly Cys Val Arg Leu Lys Arg Thr Ser Val Asn His
1               5                   10                  15

Gln Pro Asp Ala Trp Pro Glu Pro His Leu Lys Ala Ala Cys Glu Pro
            20                  25                  30

Ala

<210> SEQ ID NO 63
<211> LENGTH: 9
<212> TYPE: PRT
<213> ORGANISM: Artificial sequence
<220> FEATURE:
<223> OTHER INFORMATION: Barstar binding barnase-p3 fusion insert.
<220> FEATURE:

```
<400> SEQUENCE: 65

Leu Gln Ser Ser Gly Thr Glu Val Asp Arg Gly Asn Gln Gln His Asp
1               5                   10                  15

Thr Asn Asp Arg Asp Phe Thr His Thr Pro Leu Ser Ser Ala
            20                  25                  30

<210> SEQ ID NO 66
<211> LENGTH: 36
<212> TYPE: PRT
<213> ORGANISM: Artificial sequence
<220> FEATURE:
<223> OTHER INFORMATION: Barstar binding barnase-p3 fusion insert.
<220> FEATURE:
<221> NAME/KEY: MISC_FEATURE
<222> LOCATION: (1)..(36)
<223> OTHER INFORMATION: Barstar binding barnase-p3 fusion insert

<400> SEQUENCE: 66

Leu Gln Ser Ser Gly Val Ala Gln Gly Ser Ser Ala Ser Val Asp Val
1               5                   10                  15

Thr Ala Thr Asn Ala Val Leu Ser Ala Asp Ser Leu Ser Leu Gly Gly
            20                  25                  30

Gly Gl

```
<400> SEQUENCE: 69

Leu Gln Ser Ser Gly Val Arg Pro Ala
1               5

<210> SEQ ID NO 70
<211> LENGTH: 36
<212> TYPE: PRT
<213> ORGANISM: Artificial sequence
<220> FEATURE:
<223> OTHER INFORMATION: Barstar binding barnase-p3 fusion insert.
<220> FEATURE:
<221> NAME/KEY: MISC_FEATURE
<222> LOCATION: (1)..(36)
<223> OTHER INFORMATION: Barstar binding barnase-p3 fusion insert

<400> SEQUENCE: 70

Leu Gln Ser Ser Gly Glu Pro Ala Pro Ala His Glu Ala Lys Pro Thr
1               5                   10                  15

Glu Ala Pro Val Ala Lys Ala Glu Ala Lys Pro Glu Thr Pro Ala His
                20                  25                  30

Leu Ser Ser Ala
        35

<210> SEQ ID NO 71
<211> LENGTH: 33
<212> TYPE: PRT
<213> ORGANISM: Artificial sequence
<220> FEATURE:
<223> OTHER INFORMATION: Barstar binding barnase-p3 fusion insert.
<220> FEATURE:
<221> NAME/KEY: MISC_FEATURE
<222> LOCATION: (1)..(33)
<223> OTHER INFORMATION: Barstar binding barnase-p3 fusion insert

<400> SEQUENCE: 71

Leu Gln Ser Ser Gly Cys Val Arg Leu Lys Arg Thr Ser Val Asn His
1               5                   10                  15

Gln Pro Asp Ala Trp Pro Glu Pro His Leu Lys Ala Ala Cys Glu Pro
                20                  25                  30

Ala

<210> SEQ ID NO 72
<211> LENGTH: 36
<212> TYPE: PRT
<213> ORGANISM: Artificial sequence
<220> FEATURE:
<223> OTHER INFORMATION: Barstar binding barnase-p3 fusion insert.
<220> FEATURE:
<221> NAME/KEY: MISC_FEATURE
<222> LOCATION: (1)..(36)
<223> OTHER INFORMATION: Barstar binding barnase-p3 fusion insert

<400> SEQUENCE: 72

Leu Gln Ser Ser Gly Val Val Asp Trp Ala Lys Met Arg Glu Ile Ala
1               5                   10                  15

Asp Ser Ile Gly Ala Tyr Leu Phe Val Asp Met Ala His Val Ala Ala
                20                  25                  30

Leu Ser Ser Ala
        35

<210> SEQ ID NO 73
<211> LENGTH: 117
<212> TYPE: DNA
```

<213> ORGANISM: Artificial sequence
<220> FEATURE:
<223> OTHER INFORMATION: Vector pK1 polylinker sequence.
<220> FEATURE:
<221> NAME/KEY: misc_feature
<222> LOCATION: (1)..(117)
<223> OTHER INFORMATION: Vector pK1 polylinker sequence

<400> SEQUENCE: 73

```
aatgctggcg gcggcccagc cggcctttct gagggggtcga ctatagaagg acgaggggcc    60
cacgaaggag gtggggtacc cggttccgag ggtggttccg gttccggtga ttttgat      117
```

<210> SEQ ID NO 74
<211> LENGTH: 39
<212> TYPE: PRT
<213> ORGANISM: Artificial sequence
<220> FEATURE:
<223> OTHER INFORMATION: Polypeptide encoded by pK1 vector polylinker
      sequence.
<220> FEATURE:
<221> NAME/KEY: MISC_FEATURE
<222> LOCATION: (1)..(39)
<223> OTHER INFORMATION: Polypeptide encoded by pK1 vector polylinker
      sequence

<400> SEQUENCE: 74

```
Asn Ala Gly Gly Gly Pro Ala Gly Leu Ser Glu Gly Ser Thr Ile Glu
1               5                   10                  15

Gly Arg Gly Ala His Glu Gly Gly Val Pro Gly Ser Glu Gly Gly
            20                  25                  30

Ser Gly Ser Gly Asp Phe Asp
        35
```

<210> SEQ ID NO 75
<211> LENGTH: 117
<212> TYPE: DNA
<213> ORGANISM: Artificial sequence
<220> FEATURE:
<223> OTHER INFORMATION: Vector pK2 polylinker sequence.
<220> FEATURE:
<221> NAME/KEY: misc_feature
<222> LOCATION: (1)..(117)
<223> OTHER INFORMATION: vector pK2 polylinker sequence

<400> SEQUENCE: 75

```
aatgctggcg gcggcccagc cggcctttct gaggggtcga ctatagaagg acgagggccc    60
acgaagcagc tggggtaccg gttccgaggg tggttccggt tccggtgatt tgatta       117
```

<210> SEQ ID NO 76
<211> LENGTH: 39
<212> TYPE: PRT
<213> ORGANISM: Artificial sequence
<220> FEATURE:
<223> OTHER INFORMATION: Polypeptide sequence encoded by vector pK2
      polylinker region.
<220> FEATURE:
<221> NAME/KEY: MISC_FEATURE
<222> LOCATION: (1)..(39)
<223> OTHER INFORMATION: Polypeptide sequence encoded by vector pK2
      polylinker region.
<220> FEATURE:
<221> NAME/KEY: MISC_FEATURE
<222> LOCATION: (38)..(38)
<223> OTHER INFORMATION: X represents a TGA stop codon
<220> FEATURE:
<221> NAME/KEY: MISC_FEATURE

```
<222> LOCATION: (36)..(36)
<223> OTHER INFORMATION: X represents a stop codon (TGA)

<400> SEQUENCE: 76

Asn Ala Gly Gly Gly Pro Ala Gly Leu Ser Glu Gly Ser Thr Ile Glu
1               5                   10                  15

Gly Arg Gly Pro Thr Lys Gln Leu Gly Tyr Arg Phe Arg Gly Trp Phe
            20                  25                  30

Arg Phe Arg Xaa Phe Xaa Leu
            35

<210> SEQ ID NO 77
<211> LENGTH: 35
<212> TYPE: DNA
<213> ORGANISM: Artificial sequence
<220> FEATURE:
<223> OTHER INFORMATION: Sequence of the junction region between
      Barnase and p3 in recombinant fusion vector fd-3.
<220> FEATURE:
<221> NAME/KEY: misc_feature
<222> LOCATION: (1)..(35)
<223> OTHER INFORMATION: Sequence of the junction region between
      Barnase and p3 in recombinant fusion vector fd-3.

<400> SEQUENCE: 77
atcagactgc aggcggtgcg gccgcagaaa ctgtt                              35

<210> SEQ ID NO 78
<211> LENGTH: 11
<212> TYPE: PRT
<213> ORGANISM: Artificial sequence
<220> FEATURE:
<223> OTHER INFORMATION: Amino acid sequence about the junction of
      Barnase and p3 coding regions of recombinant fusion vector fd-3.

<400> SEQUENCE: 78

Ile Arg Leu Gln Ala Ala Ala Ala Glu Thr Val
1               5                   10

<210> SEQ ID NO 79
<211> LENGTH: 4
<212> TYPE: PRT
<213> ORGANISM: Artificial sequence
<220> FEATURE:
<223> OTHER INFORMATION: Factor Xa protease cleavage sequence.
<220> FEATURE:
<221> NAME/KEY: MISC_FEATURE
<222> LOCATION: (1)..(1)
<223> OTHER INFORMATION: X can be either Ile or Leu.
<220> FEATURE:
<221> NAME/KEY: MISC_FEATURE
<222> LOCATION: (1)..(4)
<223> OTHER INFORMATION: Factor Xa proteolytic cleavage site.

<400> SEQUENCE: 79

Xaa Glu Gly Arg
1

<210> SEQ ID NO 80
<211> LENGTH: 6
<212> TYPE: PRT
<213> ORGANISM: Artificial sequence
<220> FEATURE:
<223> OTHER INFORMATION: Artificial linker peptide.

<400> SEQUENCE: 80

Ala Gly Gly Ala Ala Ala
1               5
```

SELECTION SYSTEM

CROSS REFERENCE TO RELATED APPLICATIONS

This application is a Continuation Application of U.S. patent application Ser. No. 09/710,444, filed Nov. 10, 2000, now U.S. Pat. No. 7,442,159, which is a Continuation Application of PCT/GB99/01526, Publication No. WO99/58655 filed May 13, 1999, which claims priority to Great Britain Patent Applications GB9810233.9 and GB9810228.8 both filed on May 13, 1998. The entirety of each of the applications is incorporated herein by reference.

The invention relates to a selection system which permits the selection of polypeptides displayed in a phage display system.

Viruses have been used for the display of peptides and proteins [21, 26, 44]. In particular filamentous bacteriophage have been used for display of proteins and peptides by fusion of the genes encoding the proteins or peptides to the gene encoding a phage coat protein. As the fusion gene is encapsidated in the phage that is displaying the fusion protein, this provides a linkage of phenotype and genotype. Repertoires of proteins can be encoded by a population of phage, and the rare phage comprising proteins with predefined binding activities isolated by binding to solid phase. In this way synthetic human antibodies of predefined antigen-binding specificity have been selected from repertoires of antibody fragments assembled from different structural elements [10]. As the antibody needs to be folded to bind antigen, selection for binding also selects for folding. This principle has also been used for selection of folded peptides where binding is mediated by a discontinuous epitope [8, 11-13].

A problem present in phage display systems is the presence of high levels of background caused by the presence of phage not displaying desired polypeptides. For example, antibody repertoires are commonly encoded as fusion proteins with the p3 protein on phagemid vectors and are encapsidated by the use of helper phage. The helper phage coat protein competes with the fusion of antibody and coat protein (encoded on the phagemid), leading to phage with "monovalent" rather than multivalent display of folded antibody fragments. This can be useful in discriminating between the affinity and the avidity (with multivalent display) of the antibodies displayed on the phage. However the great majority of phages only display the helper phage coat protein which contributes to a "background" binding to antigen. In this case it is desirable to select for phages that display folded antibodies, and to eliminate those that do not.

Moreover, all of the systems in current use rely on a binding activity in the polypeptide to be selected in order to perform the isolation of the desired display bodies from those which do not encode polypeptides having a desired characteristic. This places a limitation on available display systems to the selection of folded polypeptides which possess a known binding activity. It would be desirable to have a means for selection of displayed proteins or polypeptides that is independent of the binding activity thereof.

For example, there is considerable interest in building folded proteins de novo. Attempts have been made to design proteins de novo by assembly of predefined elements of secondary structure and also from random sequences (for review [5]). In some cases the designed proteins have been shown to retain elements of secondary structure but lack the stable tertiary interactions characteristic of the folding of native proteins, suggesting the presence of molten globules (see [6] and references therein). More successful has been the creation of native-like proteins based on a pre-existing backbone [7,8]. In these cases the binding activities of a de novo designed protein will be unknown. In this case it is desirable to select for phages displaying folded proteins, and to eliminate those that do not.

Although attempts have been made to screen for folded proteins by their ability to survive degrading enzymes in bacteria [16-18], such methods do not allow for selection if bacterial growth or survival does not depend on the function of the folded protein. Thus, these systems are only applicable to a small minority of polypeptides which one might wish to select according to the ability to fold.

It has previously been shown that the insertion of a peptide sequence between a proteolytically stable tag fused to the minor phage coat protein p3 and the p3 protein itself, followed by proteolysis, provides a means to select for phages bearing peptide sequences that are susceptible to proteolysis [19, U.S. Pat. No. 5,780,279]. In these experiments, phage are bound to an affinity resin binding an N-terminal, proteolytically stable tag on the phage. If the bound phage are subjected to proteolysis and elution, only phage with cleavable sequences are eluted. This method is used to identify, among a repertoire displayed on phage, amino acid sequences suitable as substrates for proteases. The sequences introduced are short and would not be capable of folding independently. Moreover, the system selects specifically for eluted rather than bound phage; in other words, it is specifically configured to isolate cleaved rather than uncleaved phage.

SUMMARY OF THE INVENTION

The present invention exploits the application of peptide cleavage to eliminate unwanted viruses.

According to a first aspect, therefore, the invention provides a method for the selection of a virus comprising the steps of:

(a) providing a virus encoding and displaying a fusion polypeptide, said fusion polypeptide comprising a heterologous polypeptide inserted into the sequence of a viral coat protein polypeptide, wherein said virus comprises a cleavable site located within a displayed polypeptide;

(b) exposing the virus to a cleaving agent;

(c) propagating the virus comprising intact fusion protein.

According to the present invention, virus may be selected by cleavage of non-resistant virions using a cleaving agent. As used herein, “virus” refers to an infective inocculum of virions, which may incorporate cleavage sites, optionally as part of heterologous polypeptides encoded by the viral genome. Thus, “virus” may refer to a plurality of virions, such that it may encode a repertoire of polypeptides; alternatively, as the context requires, it may be used to denote a single virion. The term “virus” includes any suitable virus which may incorporate a cleavage site, either naturally or through manipulation. A preferred virus for use in the present invention is bacteriophage, preferably filamentous bacteriophage.

The term “polypeptide” is used generally to denote molecules constructed of a plurality of amino acids, the amino acids being joined together covalently such as through peptide bonds. “Fusion” polypeptides are essentially polypeptides which are incorporated into viral coat proteins, such that a fusion is created between the viral coat protein and the polypeptide in question. The fusion may incorporate the polypeptide into the viral coat protein, advantageously between domains thereof, or place it at one end thereof, to make a terminal fusion. The polypeptide is referred to as a “heterologous” polypeptide, to denote that it is heterologous to the viral coat protein into which it is inserted. It is possible, however, that it is derived from another polypeptide of said virus.

In one sense, polypeptide is used interchangeably with "protein" herein, in that no difference of structure or size is implied. Substantially any polypeptide may be selected for by the method of the present invention, including structural polypeptides, polypeptides having enzymatic activity and polypeptides having binding activity, including antibodies and antibody fragments. Cleavage sites may be present in the polypeptides, and may be naturally-occurring or may be engineered into the polypeptide or into a linker peptide attached thereto. "Polypeptide" may also refer to inserted polypeptides which are essentially non-folding polypeptides and serve to encode a cleavable site and insert this site into the coat protein of a virus. Inserted polypeptides may take the form of N- or C-terminal fusions, or may form part of the coat protein itself.

A "cleavable site" is a site capable of cleavage when exposed to a cleaving agent. In the present invention, the use of protease cleavage sites, capable of being cleaved with proteases, is preferred. Protease cleavage sites may be part of, or incorporated in, polypeptides according to the invention; alternatively, it may be independently engineered into the coat protein of the virus. A feature of the cleavable site is that it should either be absent from the virus other than at the site of its specific insertion according to the present invention, or otherwise inaccessible to cleavage, or present only in viral proteins which are not required after virion assembly to mediate infection.

In accordance with the invention, the cleavable site may be inserted into or present in any suitable position in the virus. Advantageously, however, it is inserted into or present in either the coat protein itself or the heterologous polypeptide which forms part of the fusion polypeptide.

In a preferred aspect of the present invention, more than one cleavable site may be used. For example, one site may be inserted or otherwise known to be present in the virus, whereas the presence of another site may be unknown or dependent on randomisation of the heterologous polypeptide sequence. In a particularly preferred embodiment, the cleavable sites may comprise a protease cleavable site and a bond formed through sidechains on one or more amino acids, such as a disulphide bond. Disulphide bonds are cleavable by reducing agents, such as DTT or β-mercaptoethanol.

If a virus contains a disulphide bond, cleavage of a protease cleavable site located between the two cysteine residues which form the bond through their sidechains will not lead to loss of viral infectivity since the disulphide bond is capable of retaining the covalent linkage of the viral polypeptides.

Thus, the invention further provides a method for identifying the presence of disulphide bonds in polypeptides.

Conversely, in the event that the selection of disulphide-containing polypeptides is not desired, viruses are advantageously treated with a reducing agent before or after proteolysis, in order to eliminate background due to viruses which have been cleaved by the protease but which have been held together by disulphides.

The fusion polypeptide may comprise one or more heterologous polypeptides. In the case of a terminal fusion, one such heterologous polypeptide may function as a protein tag, allowing phage which express the fusion polypeptide to be identified. The cleavable site may, in such a case, be positioned in or near the tag, such that cleavage of the cleavable site releases the tag.

A tag is any suitable entity capable of binding to a ligand which may be used to isolate a virus by the method of the present invention. Accordingly, the tag is resistant to the cleaving agent used in the method of the invention. Examples of tag/ligand pairs include barnase/barstar, avidin/biotin, antibody or antibody fragments and ligands, chelating groups and chelates, for example metals, and the like.

In all embodiments of the present invention, which are described in greater detail below, the uncleaved polypeptides are selected for; the cleaved material is discarded in the selection step.

Preferably, the virus according to the invention encode a repertoire of heterologous polypeptides. A repertoire is a collection of members, preferably polypeptides, which differ slightly from each other in a random or partially randomised manner. Preferably, a repertoire of polypeptides is a collection of variant polypeptides which preferably incorporate random or partially randomised mutations. As used herein, a repertoire preferably consist of $10^4$ members of more. A repertoire advantageously comprises a very large number of members, typically between $10^8$ and $10^{11}$, and potentially $10^{14}$ or higher.

The heterologous polypeptide, or repertoire of such polypeptides, is advantageously displayed on the surface of the virus which encodes it, by virtue of its being incorporated into a coat protein, or on the surface of cells infected by the virus. Where the virus is a bacteriophage, the protein may also be displayed on the surface of bacteria infected with the bacteriophage.

The cleavable site is advantageously located in or adjacent to the heterologous polypeptide, such that it can be protected by folding of the heterologous polypeptide and thus allow selection for heterologous polypeptides which are capable of correct folding. Alternatively, however, the cleavable site may be located distal to the heterologous polypeptide; in such embodiments, the cleavable site may serve to permit reduction of background in phage display techniques. For example, introduction of the cleavable site into helper phage used with phagemid encoding a repertoire of polypeptides allows helper phage to be removed by cleavage prior to infection of host cells, thus dramatically reducing background due to "empty" phage. Advantageously, therefore, the cleavable site is incorporated into the virus coat protein.

As referred to herein, a phagemid is a plasmid cloning vector which comprises viral replication sequences but is deficient in at least one viral function. This means that whilst phagemid may be inserted into host cells by conventional nucleic acid transfer methods, and will exist in the host cells in an episomal state, they are unable to assemble into virions and thus complete a viral cycle of infection. Helper phage are used to supply the deficient viral functions and permit the phagemid to be packaged into virions. In accordance with the invention, phagemid may encode coat protein fusions with heterologous polypeptides which incorporate a cleavable site.

Helper phage provide the viral function lacking in phagemid in order to allow packaging of the phagemid into virions. According to the invention, helper phage may be modified in order to render them cleavable by a cleaving agent, for example a protease. In one aspect of the present invention, helper phage may incorporate a coat protein having a cleavable site which, when cleaved in the "rescued" progeny phage, will render the helper phage-derived coat protein unable to mediate infection.

As will be apparent from the forgoing, in the method according to the present invention the virus which are resistant to cleavage are selected. Advantageously, the resistant virions will be selected by infection of susceptible host cells, such as bacterial host cells. Cleaved virions are not infective. Alternatively, binding of virions to a ligand, for example via a tag, is dependent on protection of a cleavable site in the virus, such that viruses which are cleaved are not isolated by ligand/tag binding.

DETAILED DESCRIPTION OF THE INVENTION

The present invention may be configured in a number of ways according to the intended procedure to which it is desired to apply the basic methodology. Selective cleavage of virions is used to reduce background in phage display techniques. By cleaving and removing phage which either do not contain a heterologous polypeptide, or express a heterologous polypeptide which is not capable of correct folding, the sensitivity of a phage display process can be increased substantially. As demonstrated in the experimental section below, using the methodology of the invention phage display may be used to select polypeptides which are not susceptible to selection by display techniques according to prior art methods.

In a first configuration, cleavage of a cleavable site in a virion coat protein may be exploited to reduce background attributable to phage displaying no heterologous polypeptides, or phage displaying heterologous polypeptides which are incapable of folding correctly. Cleavage of displayed polypeptides, in accordance with the present invention, results in the impairment of the viruses to achieve infection of host cells. Thus, by propagating viruses which have been exposed to a cleavage agent, it is possible to enrich the virus for virions which comprise displayed polypeptides which are resistant to cleavage. As used herein, "impair" means to reduce; it thus includes but partial and complete prevention of infection of host cells by affected virus.

The coat protein is selected as the site for cleavage on the grounds that it is available to cleaving agents in the host cells harbouring the virus or at the surface of the virus itself. Thus, in a preferred embodiment, virus preparations may be treated with a cleaving agent, in order to render virions having cleavable coat proteins unable to mediate infection of host cells. Alternatively, cells infected with the virus may be treated with a cleaving agent active within the cell, which will prevent packaging of virus comprising a cleavable coat protein. As used herein, the terms pIII, p3, g3 and gene III are equivalent alternative abbreviations for bacteriophage coat protein III.

According to the present invention, reference to selection may be interpreted as a reference to screening, since the same processes may be used to screen phage, as will be apparent to persons skilled in the art.

Cleavable sites may be naturally part of the coat protein, but preferably they are engineered therein. Preferred cleavable sites include protease cleavage sites, which may be found in polypeptides or engineered as an integral part of their sequence. Typically, protease cleavage sites may be defined in terms of amino acid sequences which are susceptible to cleavage by a protease. For example, the invention encompasses the use of protease cleavage sites cleavable by one or more of the proteases trypsin (cleaves at Lys, Arg), chymotrypsin (Phe, Trp, Tyr, Leu), thermolysin (small aliphatic residues), subtilisin (small aliphatic residues), Glu-C (Glu), Factor Xa (Ile/Leu-Glu-Gly-Arg), Arg-C (Arg) and thrombin.

Protease cleavage sites may be incorporated into the coat protein of a virus by constructing a fusion between the coat protein and a further polypeptide, the further polypeptide containing the cleavage site. The further polypeptide should be inserted at a position in the viral coat protein such that it allows the assembly of a functional viral capsid and subsequent infection, but if cleaved will result in the impairment of infectivity.

If the protease cleavage site incorporated in the coat protein remains uncleaved, therefore, the virus is capable of assembly into functional virions and retains the potential to infect host cells. If the protease cleavage site is cleaved, however, the structure of the viral coat protein will be compromised and the virus will lose at least part of its potential to infect host cells.

In a preferred embodiment, the virus for use in the present invention is a bacteriophage, preferably filamentous bacteriophage. Filamentous bacteriophage is widely used in phage display techniques for the selection of polypeptides from phage libraries encoding a large repertoire thereof. Conventionally, the repertoire of polypeptides is inserted in the p3 protein of filamentous bacteriophage, but any other suitable site may be employed within the scope of the present invention.

In the case of the p3 protein of filamentous bacteriophage the protein consists of three domains. The N-terminal D1 is involved in binding to the tolA receptor, D2 in binding to the F-pilus (and mediating infection) and D3 in anchoring the protein to the phage particle. Peptides and proteins can be inserted at the domain boundaries without abolishing infectivity [21, 22], but the presence of all the domains is essential for phage infectivity [23]. The bacteriophage are resistant to proteolysis (allowing their use as "substrate" phage, [19]), but the introduction of polypeptides comprising protease cleavage sites into p3, for example at the junctions between domains leads to loss in infectivity of the phage upon proteolysis.

The protease cleavage sites may be incorporated into heterologous polypeptides. As described above, heterologous polypeptides may be encoded in the form of a repertoire in a phage library. As folded polypeptides or proteins are often resistant to proteolysis and unfolded proteins are sensitive, cleavage requires the polypeptide chain to bind and adapt to the specific stereochemistry of the protease active site, and therefore to be flexible, accessible and capable of local unfolding [14, 15]. The cloning of a polypeptide comprising protease cleavage sites at the domain junctions of p3, followed by proteolysis, provides a means of selection for phages bearing proteins that are resistant to proteolysis and are folded.

In the case of phage display repertoires (wherein the polypeptide to be selected is cloned at the N-terminus of p3) encoded on phagemid vectors, the use of helper phage comprising a polypeptide comprising protease cleavage sites at the domain boundaries, followed by proteolysis, provides a means of selection for phages that display the fusion protein by eliminating the helper phage after the "help" has been given.

The use of the protease-cleavable helper followed by protease cleavage selects for phages bearing the fusion protein (and for good display). As many phages in a repertoire do not display fusion proteins [26] and these contribute to non-specific binding of the phage, this should also improve selection efficiencies. When using the techniques of the prior art, only between 0.1-1% of all phage particles in a phage library may comprise a gene 3 protein arising from the phagemid. Therefore the majority (99-99.9%) of phage particles that have bound non-specifically to the solid support used in selection will comprise p3 from the helper phage (irrespective of the genome carried by the phage particle which most likely will be a phagemid DNA), these particles are rendered non-infective by proteolytic cleavage.

According to a third embodiment, the selection process may be used for identification of interacting protein elements. If two such elements linked by a polypeptide comprising protease cleavage sites are cloned between the D2 and D3 domains for display on phage, the only infectious phages after proteolysis are those in which the D2 and D3 domains are held together by non-covalent interactions between the interacting protein elements. The invention accordingly permits selection of a repertoire of polypeptides for its ability to interact with a selected polypeptide, or a second repertoire of polypeptides. Unlike the two-hybrid system, the invention relies on dissociation of non-interacting elements as distinct from the association of interacting elements for the selection step. Moreover, the invention permits the harnessing of the power of phage display to greatly increase the degree of selection.

The invention optionally comprises the use of conditions or agents, during cleavage of the cleavable site, which modulate the liability of the cleavage site in the presence of the cleaving agent. This approach may be used to increase cleavage, for example to select only for polypeptides which fold in such a manner as to closely shield the cleavable site from access by the cleaving agent, or to decrease cleavage, for example to select stable mutants from a repertoire of polypeptides which is ordinarily relatively labile under cleavage conditions.

For example, modulation of the liability of the cleavable site may be achieved by the use of agents which increase or decrease such liability. Thus, a protein denaturant may be included, at a suitable concentration, to destabilise a polypeptide and render it more labile. Alternatively, a ligand for a polypeptide may be included. The ligand may stabilise the folded structure of the polypeptide, rendering it less sensitive to cleavage. Alternatively the ligand may destabilise the folded structure of the polypeptide, for example by favouring the adoption of an alternative configuration. This may render the polypeptide more accessible to the cleavage agent, and thus more labile.

In a further embodiment, the conditions of the cleavage process may be altered, such as by manipulating the pH or the temperature at which cleavage is conducted, to achieve similar effects. Thus, deviation of the pH from the optimum for the polypeptide comprising the cleavable site may cause the site to become more accessible to the cleaving agent. Similarly, raising (or lowering) the temperature of the conditions under which the polypeptide is cleaved may render the polypeptide more or less susceptible to cleavage.

In some instances, non-covalent interactions may be responsible for peptides retaining their structure and coat proteins remaining viable, even after successful cleavage of the cleavable site. The use of denaturants, temperature variation and other potentially destabilising techniques may also be used to decrease the likelihood of a cleaved polypeptide retaining its structure.

Proteolytic selection for protein folding may be applied in a number of areas, as it allows much larger numbers of proteins to be processed than with conventional screening. For example, it allows the isolation of mutant proteins with improved stability [1], for example from combinatorial libraries of mutants in which residues at several sites are varied simultaneously [39, 40] or from random mutants or by recombination [3, 4]. It also allows the isolation of novel proteins and architectures from large repertoires of sequences [16-18, 41]; and for improvement in folding stability over several rounds of mutation and increasingly stringent selection, much like the affinity maturation of antibodies.

A second configuration of the present invention concerns the use of tags to allow isolation of correctly folded heterologous polypeptides, exploiting the ability of correctly folded polypeptides to protect a cleavable site on to or near to an associated tag. The insertion of a polypeptide between the stable tag fused to the N-terminus of the viral coat protein and the coat protein itself, followed by cleavage, provides a means of selection for virus bearing proteins that are resistant to proteolysis and are folded. Thus only virions, whose inserted polypeptide is not degraded, will keep the tag fusion as part of their coat, and only these virions can therefore be captured by affinity purification using this tag. After elution the affinity captured phases from the ligand, these phages can be propagated and subjected to further rounds of the same selection procedure.

Alternatively, virions may be bound to an affinity matrix, comprising a ligand for the tag, prior to cleavage. The cleaving agent may subsequently be added, and only resistant phage will be retained on the matrix. These may then be eluted as required.

Suitable matrices include columns, beads and other surfaces to which a ligand for the tag is bound.

According to the present invention, reference to selection may be interpreted as a reference to screening, since the same processes may be used to screen phage, as will be apparent to persons skilled in the art.

Cleavable sites are substantially as described for the previous configuration of the present invention and are advantageously protease cleavable sites.

Cleavage requires the polypeptide chain to bind and adapt to the specific stereochemistry of the protease active site, and therefore to be flexible, accessible and capable of local unfolding [14, 15]. Folded polypeptides or proteins are often resistant to proteolysis, due to a relative inflexibility in their structure, whilst unfolded proteins remain sensitive.

As referred to above, the possible selection of polypeptides from a repertoire which, through variation or mutation, do not contain a recognition sequence for any particular protease used in this method, can be circumvented in two ways. For example, the use of a cocktail of proteases with very distinct recognition sequences would ensure that all polypeptides should be cleavable, if not protected by their folded status. Alternatively, a phage repertoire of polypeptides to be selected could be partially denatured, such that the inserted polypeptide unfolds but the phage and the N-terminal tag remains intact. Proteolytic digestion followed by affinity purification would remove all phages from the repertoire, which have escaped proteolysis due to the lack of protease recognition sequences in the polypeptide. Phages not bound by the resin, contain only phages, which contain the protease recognition sequence in the polypeptide displayed and which may or may not escape proteolysis under non-denaturing conditions. Thus these would be subjected to proteolytic selection based on protection by the folding status of the polypeptide displayed.

The selection process may also be used for the identification of interacting protein elements. Thus if two such elements linked by a polypeptide comprising protease cleavage sites are cloned between the N-terminal, proteolytically stable tag for display on phage and the coat protein, the only phages after proteolysis, that can be captured via affinity binding to the tag, are those in which the tag and the p3 protein are held together by non-covalent interactions between the interacting protein elements.

The invention is further described in the following examples, for the purposes of illustration only.

Example 1

Resistance of Filamentous Phage to Proteolysis

Materials and Methods for Examples 1-6 are appended at the end of Example 6.

Phage is incubated under a range of denaturing conditions in vitro and then restored to native conditions immediately before infection of bacteria. The incubation of phage in 10 M urea, or extremes of pH (as low as pH 2, and as high as pH 12) and temperature (as high as 60° C.) did not lead to a major loss of infectivity (Table 1). This indicates that the phage is either resistant to denaturing conditions or that if it does unfold it is able to refold rapidly. However with guanidine hydrochloride (GndHCl) a 5 fold loss in phage infectivity is observed above 5 M and a further 5 fold loss at 8 M (Table 1).

Phage is then incubated under native conditions with a range of proteases (trypsin, Factor Xa, IgA protease, Asp-N, chymotrypsin, Arg-C, Glu-C, thrombin, thermolysin, subtilisin) with different specificities. There is no loss in infectivity except for subtilisin which has been reported to cleave the p3 protein [24]. If phage is incubated under denaturing conditions in the presence of proteases such as trypsin in 3.5 M urea (or >47° C.), infectivity is lost. This indicates that under denaturing conditions the unfolding of the phage coat proteins is sufficient to make sites available for proteolysis.

Example 2

Construction of Phage with Protease Cleavage Sites

A sequence (PAGLSEGSTIEGRGAHE, SEQ ID NO: 1) comprising several proteolytic sites is inserted in the flexible glycine-rich region between the D2 and D3 domains of the phage p3.

Incubation of the phage (fd-K108) under native conditions with trypsin, thermolysin or subtilisin now resulted in almost complete loss of infectivity (from $10^7$ to <10 TU/ml) and incubation with Glu-C and chymotrypsin resulted in a major loss (from $10^7$ to $10^4$ TU/ml). This indicates that these proteases cleave the new linker. However incubation with Factor Xa, Arg-C or thrombin did not lead to a loss in infectivity, despite the presence of potential cleavage sites for these enzymes. Presumably the presence of the D2 and D3 domains may block access or cleavage for these enzymes in the case of the present polypeptide.

Example 3

Construction of Protease Cleavable Helper Phage and Phagemid

Fusion of proteins to p3 should lead to multivalent display of the protein on the phage. However if the protein is fused to p3 encoded by a phagemid (such as pHEN1 [25]), and the bacteria harbouring the phagemid is rescued with a helper phage (such as VCSM13), the fusion protein has to compete for incorporation into the phage with the helper p3. This leads to so-called "monomeric" phage, in which usually less than one copy of the fusion protein is attached to each phage particle [26].

The use of "monomeric" phage might be expected to be advantageous for selection of high affinity interactions. Furthermore fusion proteins in "monomeric" phage should be more sensitive to proteolysis, as interactions between multimers of fusion protein are avoided. However a disadvantage is that the majority of infective phages do not display a protein; such phages binding non-specifically to solid phase are amplified during each round of phage growth.

Protease cleavable helper phage are therefore constructed, by introducing the protease cleavage sequence between the D2 and D3 domains to generate the helper phage KM13.

TABLE 1

Stability of wild type fd-DOG under different conditions.

| Urea (60° C., 90 min) | | | | | |
|---|---|---|---|---|---|
| Control | 2 M | 4 M | 6M | 8 M | 10 M |
| 0.56 | 0.64 | 0.32 | 0.32 | 0.80 | 068 |
| GndHCl (37° C., 90 min) | | | | | |
| Control | 2 M | 4 M | 5 M | 6 M | 7 M | 8 M |
| 0.72 | 0.60 | 0.70 | 0.16 | 0.13 | 0.16 | 0.03 |
| pH (37°, 30 min) | | | | | |
| Control | pH 2.2 | pH 4.0 | pH 7.4 | pH 10 | pH 12 |
| 1.5 | 0.46 | 1.3 | 1.5 | 1.4 | 0.40 |
| Temperature (30 min) | | | |
| Control | 22° C. | 37° C. | 60° C. |
| 9.7 | 8.3 | 9.6 | 12.0 |

The infectivity (TU/ml × $10^{10}$) was measured (see Materials and Methods) and has an estimated error of about ±6%.

KM13 is shown to rescue the phagemid pHEN1. Furthermore trypsin is shown to cleave a major fraction (about 50%) of p3 of the rescued phage as shown by Western blot and detected with an anti-D3 mAb (FIG. 1). However phage infectivity is hardly altered by the cleavage; it therefore appears that only a fraction of the p3 need be entire to mediate bacterial infection.

KM13 is also shown to rescue a pHEN1 phagemid encoding a single chain antibody fragment [27]. Here cleavage by trypsin resulted in a 50 fold loss in phage infectivity (data not shown), consistent with indications that only a small fraction of the phage express fusion protein when rescued with helper phage [26, 28].

A protease cleavable phagemid is also constructed. The phagemid can be rescued with KM13 or VCSM13. As expected, infectivity of this phagemid rescued with KM13 (but not VCSM13) is destroyed by trypsin. This phagemid vector is prone to deletions in the D2-D3 linker; by changing the codon usage in the linker regions on either site of the protease cleavable site, and shortening the length of these linker regions, a more stable vector is created (pK1; FIG. 2). In a second vector (pK2; FIG. 2), the sequence of the polylinker is arranged so as to place D3 out of frame to render religations within the polylinker non-infectious.

Example 4

Construction of a Phage Antibody Library Using Protease Cleavable Helper Phage Bacteria are electroporated with phagemid DNA encoding a repertoire of scFv fragments fused to the N-terminus of p3 and grown in liquid culture (2×TY containing antibiotic to select for bacteria containing phagemid and glucose to suppress expression of gene 3). In the mid log phase of bacterial growth (OD600=0.5) the helper phage KM13 is added to the bacteria to give a ratio of helper phage to bacteria of 20:1. The bacteria is incubated at 37° C. without shaking for 45 min then with shaking for 45 min. The bacteria are harvested by centrifugation and resuspended in fresh medium containing 50µ/ml kanamycin and antibiotic, without glucose, to select for presence of phagemid DNA. The culture is grown overnight at 30° C. with shaking.

Bacteria are removed from the phage containing supernatant by centrifugation. Phage is precipitated from the supernatant by adding ⅕ the volume of 20% PEG/2.5 M NaCl. After 1-2 hours at 4° C. the precipitated phage is collected by centrifugation. The phage is resuspended in PBS (a second PEG precipitation is optional) and can be used in selection.

The library of phages is allowed to bind to antigen (immobilised on solid support such as an immunotube or in solution to tagged (i.e. biotinylated) antigen which can be immobilised after affinity binding of phage antibodies). Unbound phage is removed by extensive washing (the stringency of washing can be varied with respect to time and detergents added).

Phage libraries comprising a cleavable tag, such as the c-myc tag inserted between the antibody and gene 3, can be eluted by addition of trypsin in solution at a concentration of 0.1 to 1 mg/ml. (Phage libraries without a cleavable sequence between the antibody and gene 3 can be eluted by adding 100 mM Triethylamine. In this case the solution is neutralised by adding 1 M Tris-HCl pH 7.4. and after 10 min, trypsin added to a final concentration of 0.1 to 1 mg/ml.) Trypsin also cleaves the copies of gene 3 from the helper phage, while leaving gene 3 from the phagemid intact. Thus only phage that had carried, or still carry, an antibody fusion will be infective.

Phage is used to infect bacteria in mid log phase of growth (OD600=0.5), and the bacteria is plated on agar plates containing antibiotic selecting for phagemid DNA. Individual clones were picked and phage prepared as above. The resulting phage is used in ELISA to identify phage antibodies binding specifically to the antigen of interest.

Example 5

Selection for Folding Using Barnase as a Model

Barnase is a small RNase of 110 amino acid residues whose folding has been extensively studied (for review [2]). Barnase contains multiple sites for trypsin cleavage, although the folded protein is resistant to cleavage (data not shown). Phage with barnase cloned between D2 and D3 should therefore be resistant to protease cleavage and capable of selection.

As barnase is toxic to *Escherichia coli*, a mutant A (His 102->Ala) is cloned which is catalytically inactive but stable [29, 30] into the phagemid pK2. A mutant B (His102->Ala, Leu14->Ala) is also cloned, with lower stability; Leu14 is buried in the hydrophobic core and its mutation creates a large cavity in the core affecting the packing of different structural elements [31]. The phages (rescued with KM13) bind to the inhibitor barstar by ELISA (FIG. 3), and therefore display the mutant barnase in a folded form.

The phages are then incubated with trypsin at a range of temperatures (FIG. 4). After incubation at 10° C., there is a decrease in phage infectivity of 5 to 10 fold for both mutants, suggesting that (as above with the display of scFv fragment) only a small fraction of the phages display the fusion protein. There is no further loss in infectivity on cleavage until 30° C. (for mutant B) or 37° C. (for mutant A). In both cases the major transition is at least 10° C. below that expected for the reversible thermal unfolding of the mutants.

Phages A and B are mixed in different ratios and incubated with trypsin at 20° C., where both mutants are stable to cleavage, or at 37° C. where only A is stable. After "proteolytic selection" the phages are plated and analysed by PCR, which is followed by restriction digest to distinguish the mutants. As shown in the Table 2, mutant A is enriched by a factor of $1.6 \times 10^4$ after a single round and by $1.3 \times 10^6$ after two rounds of proteolytic selection at 37° C. No enrichment can be detected at 20° C.

Example 6

Selection for Folding Using Villin as a Model

The 35 amino acid subdomain of the headpiece domain of the f-actin-bundling protein villin [32] is much smaller than barnase. It nevertheless forms a stable fold at room temperature and is resistant to proteolysis; furthermore its stability does not rely on disulphide bonds or binding ligands [33]. The villin subdomain (which contains several potential trypsin cleavage sites) is cloned between the D2 and D3 domains of the phage, and incubated with trypsin at different temperatures. The profile for loss of infectivity is not as sharp as with barnase, with the major transition below 35° C., considerably below the thermal unfolding of villin (70° C.) [32, 33]. The phage displaying villin are mixed with phage, which were produced using the phagemid pK1 and the helperphage KM13, and incubated with trypsin. After a single round of proteolytic selection, the villin fusion phage are enriched $8.7 \times 10^3$ fold (Table 3).

In summary, the results from Examples 1 and 2 show that the infectivity of the phage is relatively resistant to temperature, pH, urea and GndHCl, and to several proteases, but if a flexible linker comprising a protease cleavage site is inserted between domains D2 and D3 of the phage coat protein p3, the phage becomes sensitive to cleavage. By contrast, as shown in Examples 5 and 6, if the protease cleavage sites comprise a folded protein domain such as barnase or villin, the phage is resistant to cleavage. This allows proteolytic selection for protein folding, with enrichment factors of greater than $10^4$ fold for a single round of selection. Selection is evident for both for barnase, an average sized [34] domain of 110 amino acids and for villin, a small domain of 35 amino acids.

Discrimination between structures of different stabilities can be accomplished by increasing the stringency of proteolytic selection. Thus with increase in temperature, both barnase and villin became susceptible to cleavage, reflecting protein unfolding. However the main impact of protease cleavage is at a temperature lower than the unfolding transition as measured by circular dichroism [38]. This may reflect the fact that the unfolding transition is a fully reversible process, whereas the cleavage by proteases (of unfolded structure) is a kinetic and irreversible process, pulling over the equilibrium from folded to unfolded (and cleaved) structure. This is consistent with the CD unfolding transition seen with villin [33], where at temperatures as low as 35° C. there is evidence of unfolding, the same point at which villin starts to become susceptible to protease attack.

TABLE 2

Selection of Barnase mutants.

| | | Phage A:Phage B | | | | |
|---|---|---|---|---|---|---|
| | | $1.1^a$ | $1:10^2$ | $1:10^4$ | $1:10^6$ | $1:10^8$ |
| Round 1 | Phage A | 16 ($14^b$) | 24 | 20 | 0 | nd |
| | Phage B | 8 ($10^b$) | 0 | 4 | 24 | nd |
| | Enrichment | — | — | $1.6 \times 10^4$ | — | nd |
| Round 2 | Phage A | nd | nd | nd | 24 | nd |
| | Phage B | nd | nd | nd | 12 | 36 |
| | Enrichment | nd | nd | nd | $1.3 \times 10^6$ | — |

TABLE 2-continued

Selection of Barnase mutants.

| | Phage A:Phage B | | | |
|---|---|---|---|---|
| 1:1[a] | 1:10² | 1:10⁴ | 1:10⁶ | 1:10⁸ |

Mixtures of barnase mutants (A + B) in ratios from 1:1 to 1:10⁸ were selected by proteolysis at 37° C., 24 (or 36 in round 2) phage clones analysed and numbers of each mutant noted above.
[a] Selection at 20° C. where both mutants are expected to be stable.
[b] before selection.

TABLE 3

Selection of villin.

| | 1:1 | 1:10² | 1:10⁴ | 1:10⁶ |
|---|---|---|---|---|
| pK1 | 0 (16[a]) | 0 | 7 | 24 |
| Villin | 24 (8[a]) | 24 | 17 | 0 |
| Enrichment | — | — | 8.7 × 10³ | — |

Mixtures of villin-phage and pK1 rescued with KM13 in ratios from 1:1 to 1:10⁶ were selected by proteolysis at 10° C., 24 phage clones analysed and number of each noted above.
[a] before selection.

TABLE 4

| Primer sequences | |
|---|---|
| Pklinker | 5' GGCACCCTCAGAACGGTACCCCACCCTCAGAGG CCGGCTGGGCCGCCACCCTCAGAG 3' (SEQ ID NO: 2) |
| polyXafor | 5' GGTGGCGGCCCAGCCGGCCTTTCTGAGGGGTCG ACTATAGAAGGACGAGGGCCCAGCGAAGGAGGTGGG GTACCCCCTTCTGAGGGTGG 3' (SEQ ID NO: 3) |
| polyXaback | 5' CCACCCTCAGAAGGGGGTACCCCACCTCCTTCG CTGGGCCCTCGTCCTTCTATAGTCGACCCCTCAGAA AGGCCGGCTGGGCCGCCACC 3' (SEQ ID NO: 4) |
| fdPCRBack | 5' GCGATGGTTGTTGTCATTGTCGGC 3' (SEQ ID NO: 5) |
| LIBSEQfor | 5' AAAAGAAACGCAAAGACACCACGG 3' (SEQ ID NO: 6) |
| LIBSEQback | 5' CCTCCTGAGTACGGTGATACACC 3' (SEQ ID NO: 7) |
| LSPAfor | 5' GTAAATTCAGAGACTGCGCTTTCC 3' (SEQ ID NO: 8) |
| LSPAback | 5' ATTTTCGGTCATAGCCCCCTTATTAG 3' (SEQ ID NO: 9) |
| Flagprimer | 5' CAAACGGGCGGCCGCAGACTACAAGGATGACGA CGACAAGGAAACTGTTGAAAGTTGTTTAGCAA 3' (SEQ ID NO: 10) |
| RECGLYfor | 5' CCCCTCAGAAAGGCCGGCTGGGCCGCCGCCAGC ATTGACAGGAGGTTCAGG 3' (SEQ ID NO: 11) |
| RECGLYback | 5' GAAGGAGGTGGGGTACCCGGTTCCGAGGGTGGT TCCGGTTCCGGTGATTTTG 3' (SEQ ID NO: 12) |
| delCKpn | 5' CCCTCGGAACCGGTACCCCAGCTGCTTCGTGGG CCC 3' (SEQ ID NO: 13) |
| Barnasefor | 5' CTGGCGGCGGCCCAGCCGGCCCTGCACAGGTTA TCAACACGTTTGAC 3' (SEQ ID NO: 14) |

TABLE 4-continued

| Primer sequences | |
|---|---|
| BarnaseH102Aback | 5' CTCGGAACCGGTACCTCTGATTTTTGTAAAGGT CTGATAAGCG 3' (SEQ ID NO: 15) |
| villinfor | 5' GGCGGCCCAGCCGGCCTTTCTCTCTCTGACGAG GACTTCAAGGC 3' (SEQ ID NO: 16) |
| villinback | 5' CCTCGGAACCGGTACCGAAGAGTCCTTTCTCCT TCTTGAGG 3' (SEQ ID NO: 17) |

Materials & Methods (Examples 1-6)

Materials

All restriction enzymes, T4 ligase are obtained from New England Biolabs. Taq DNA polymerase is obtained from HT Biotechnology. Pfu DNA polymerase is obtained from Stratagene. Ultrapure dNTP from Pharmacia. Proteases and the protease inhibitor PEFABLOC™ are obtained from Boehringer Mannheim, except chymotrypsin and trypsin TPCK-treated which are obtained from Sigma. All other chemical are likewise obtained from Sigma.

Phage Preparation

*Escherichia coli* TG1 [42] is used for cloning and propagation of phage. TG1 harbouring fd-DOG [43] or derivatives is grown overnight in 2×TY containing 15 μg/ml tetracycline. Phagemids are rescued using KM13 or VCSM13 as described [27]. Phage particles are prepared by two PEG precipitations [44].

Vector Construction

The phage vector fd-DOG [43] is used as parent vector for construction of the protease cleavable fd-K108. Unique restriction sites (SfiI, KpnI) are introduced into the glycine rich spacer region between D2 and D3 using the SCULPTOR™ in vitro mutagenesis system (Amersham) and the oligonucleotide pklinker (Table 4). Further restriction sites (ApaI, SalI) and sequence encoding a protease cleavage site are cloned between the SfiI and KpnI sites using the oligonucleotides polyxafor and polyxaback to create the vector fd-K108.

The protease cleavable helper phage KM13 is prepared from fd-K108 by transplanting into the helper phage VCSM13 a BamH1-ClaI fragment generated by PCR and primers fdPCRBack and LIBSEQfor.

A protease cleavable phagemid vector is derived from fd-K108 much as above except using pCANTAB 3 (Pharmacia). A FLAG-tag is introduced at the N-terminus of D1 by cloning of a NotI-SfiI fragment generated by PCR and primers Flagprimer and LSPAback. To circumvent deletions due to repeated sequence in the D2-D3 linker, the codon usage of the polylinker region is changed in two steps (a) using a Bam-SfiI fragment generated by PCR and primers RECGLYfor and LIBSEQfor, screening recombinants by PCR and the primers LSPAfor and LSPAback, (b) using a KpnI-ClaI fragment generated by PCR and the primers RECGLYback and LIBSEQback, screening recombinants using LSPAfor and LSPAback. The resulting vector is pK1. The entire p3 gene is sequenced using PCR cycle sequencing with fluorescent dideoxy chain terminators (Applied Biosystems) [45]. The "out of frame" vector pK2 is derived from pK1 by site direct mutagenesis using the oligo delCKpn and the SCULPTOR™ in vitro mutagenesis system (Amersham) kit. The precise sequences of pK1 and pK2 are set forth in Kristensen et al., (1998) Folding & Design 3: 321-328.

Cloning of Barnase and Villin

The vectors encoding the single barnase mutants, His102->Ala and Leu14->Ala [29, 46] are used as templates for PCR amplification with primers Barnasefor and BarnaseH102Aback and Pfu polymerase. The PCR products (encoding the single mutant His 102->Ala, and the double mutant His 102->Ala, Leu14->Ala) are digested using the restriction enzymes SfiI and KpnI, and ligated into vector pK2 to give the phagemids pK2BA and pK2BB respectively and the barnase genes sequenced using PCR cycle sequencing.

The 35 amino acid thermostable fragment of the headpiece of the f-actin binding protein villin [33] is amplified from chicken bursa cDNA using PCR primers villinfor and villinback with Pfu polymerase. The PCR products are cloned as above to give the phagemid pK2V.

Resistance of Phages to Denaturants, pH and Proteases

For resistance to denaturants, 10 M urea in PBS (25 mM $NaH_2PO_4$, 125 mM NaCl pH 7.0) or 8 M GndHCl (Guanidine hydrochloride) and 50 mM Tris-HCl pH 7.4, 1 mM $CaCl_2$ (buffer A) is added to 10μ21 phage stocks ($10^8$-$10^{10}$ TU) to give a volume of 1 ml and the conditions specified in Table 1. The phage are incubated for 1-2 hrs, then 100 μl aliquot added to 1 ml TG1 (OD600~0.5) and serial dilutions plated on TYE plates with 15 μg/ml tetracycline. For resistance of phage to extremes of pH (2-12), Tris glycine or Tris HCl buffers (0.1 M glycine or 0.1 M Tris respectively) are added to 10 μl phage stocks, and to neutralise each 100 μl aliquot we added 50 μl 1 M Tris-HCl pH 7.4 before infection. For resistance to temperature, buffer A is added to 10 μl phage stocks to give a volume of 1 ml and incubated at a given temperature (20-60 C) for 1 hr. 100 μl aliquots are added to TG1 and plated as above. For resistance to proteases, 100 mM NaCl, 50 mM Tris-HCl, 1 mM $CaCl_2$ pH 7.4 (Factor Xa 100 ng/ml or trypsin, chymotrypsin, thrombin, thermolysin and subtilisin all 100 μg/ml) or 50 mM Tris-HCl, 1 mM EDTA pH 7.4 (IgA Protease 10 ng/ml) or 50 mM $NH_4CO_3$ pH 8.0 (Arg-C100 μg/ml, Glu-C 100 μg/ml) or 25 mM $NaH_2PO_4$, 125 mM NaCl pH 7.0 (AspN 40 ng/ml) is added to 10 μl phage stocks (fd-DOG and fd-K108) to give a volume of 100 μl and a final concentration of protease as indicated. Digestions are incubated for 15 min at room temperature, samples (100 μl) are then infected into TG1 as above.

For resistance to proteases in the presence of denaturants samples are prepared as above for urea and temperature denaturation. To 90 gl aliquots 10 121 trypsin (1 mg/ml) is added, after 5 mM at room temperature 4 Al PEFABLOC™ protease inhibitor (100 mM) is added and the samples are infected into TG1 as above.

Western Blot

Phages (pHEN1 rescued using KM13 and pK1 rescued using VCSM13) are subjected to SDS-PAGE [47] before or after cleavage by trypsin (50 ng/ml). After semidry transfer to PVDF membranes the filter is process essentially as described [27]. The primary antibody, monoclonal anti-gill (MoBiTec), is added in a 1:5000 dilution followed by antimouse HRP-conjugated antibody (Sigma) in a dilution of 1:50000. Finally the filter is developed using the luminol based Chemiluminescence Western Blotting kit (Boehringer Mannheim).

ELISA

Phage displaying barnase mutants are analysis for binding to the RNase inhibitor barstar as described [44]. 10 pmol biotinylated barstar is mixed with approximately $10^{10}$ phage displaying barnase mutant A or barnase mutant B or villin or buffer A. Phage binding barstar is captured on Streptavidin coated plates (Boehringer Mannheim) and developed using HRP conjugated anti-M13 antibody (Pharmacia) and 2,2'-Azino-Bis(3-Ethylbenzthiazoline-6-sulfonic acid) (Sigma). Absorbance readings are taken at 405 nm.

Temperature Denaturation

At each temperature approximately $10^{10}$ phage displaying the barnase mutants or villin (ampicillin resistant) is mixed with a cleavable control fd-K108 (tetracycline resistant), and a non-cleavable control phagemid, a chloramphenicol resistant derivative of pHEN1, rescued with KM13 in a total volume of 90 μl of buffer A. After equilibration for 20-30 min at the temperature indicated, 10 μl trypsin (5 μg/ml) is added and the incubation continued for 2 min. Trypsin is neutralised by adding 4 μl 100 mM PEFABLOC™ protease inhibitor. Infection and serial dilution is performed in TG-1 as above and aliquots are plated on TYE plates containing 100 μg/ml ampicillin+1% glucose, 30 μg/ml chloramphenicol+1% glucose or 15 μg/ml tetracycline.

Selection Experiments

10 μl of serial dilutions of the barnase mutant phage A is mixed with 10 μl of the non-diluted barnase mutant phage B in 70 μl buffer A. After 30 min incubation at 20° C. or 37° C. 10 μl trypsin (5 μg/ml) is added. Following 2 min. of digestion 4 μl PEFABLOC™ protease inhibitor (100 mM) is added. The phage are infected into TG1 as above. A second round of selection are performed by scraping bacteria in 3 ml 2×TY, 50 μl inoculated into 50 ml 2×TY/Amp/Glu and the phagemid rescued and phage prepared as above. Clones are analysed by PCR using the primers LSPAfor and LSPAback followed by restriction digestion using DdeI.

Selections between pK2V and pK1 phage particles are performed as above, except the selection is performed at 10° C. Clones are analysed by PCR using the primers LSPAfor and LSPAback.

Example 7

Use of Protease-Cleavable Helper Phage for Selection of Signal Sequences

Translocation of proteins is directed by signal peptides [48]. These are known to share common features such as a positively charged amino-terminal region, a hydrophobic sequence and a carboxy-terminal region including the signal peptidase cleavage site. Signal peptides are involved in "an array of protein-protein and protein-lipid interactions" [49]. The signal sequence may in addition interfere with the protein folding pathway. They are also involved in translational regulation, mainly through the downstream box.

Enzymes such as DNA polymerase are very poorly displayed on phage particles, making their selection almost impossible. In order to improve the capabilities of phage display to select polymerases, therefore, improved signal sequences are designed and selected for using a phage display technique in which "empty" phage background is eliminated by digestion of helper phage.

Design of a signal sequence for optimal polymerase display on phage is not easily achieved. A selection strategy is therefore devised to isolate signal sequences from a library where mutations are introduced at selected sites. Although the signal sequence is not present on phage, its sequence is easily retrieved by sequencing the phagemid located within the phage particle.

Two libraries are generated from pelB and g3 leader sequences, making use of the following oligonucleotide primers for PCR amplification:

```
1:  TACGCCAAGCTTGCATGC;                     (SEQ ID NO: 18);
2:  CTGCACCTGGGCCATGG;                      (SEQ ID NO: 19);
3:  GATTACGCCAAGCTTTG;                      (SEQ ID NO: 20);
4:  GATTACGCCAAGCTTGCATGCANNDDCTNTD         (SEQ ID NO: 21);
    TCAAGGAGACAGTCATAATGARRNNBCTATT
    GSYAAYRSYASYASYAGBNTTGTTATTACTC
    SYANYCVNNCYGDCCATGGCCCAGGTGCAGC
    TG;
5:  GATTACGCCAAGCTTTGNNNNCTTTTTTWWG         (SEQ ID NO: 22)
    GAGATTTTCAACRTGARAARATTATTATTCS
    YAATTSYTTTAGTTSYTSYTTTCTWTGYGGY
    CCAGCCGGCCATGGCCCAGGTGCA.
6:  CTTTATGCTTCCGGCTCG.                     (SEQ ID NO: 23)
7:  CGGCCCCATTCAGATCC.                      (SEQ ID NO: 24)
```

The restriction sites HindIII and NcoI are noted in italics.

Library I deriving from the pelB leader and library II deriving from the g3 leader are prepared by PCR amplification of 4 (pelB) amplified with 1 and 2 and of 5 (g3) amplified with 3 and 2 respectively. Each PCR product is digested with HindIII and NcoI and purified with a gel extraction kit (Qiaquick, Qiagen). 0.2 µg of each resulting insert is mixed for ligation with about 2 µg of pHEN1-Stoffel vector (FIG. 6) previously digested with HindIII and NcoI and dephosphorylated with alkaline phosphatase (Boehringer Mannheim). The ligation mixture is purified by phenol-chloroform extraction and ethanol precipitation prior to electroporation into freshly prepared E. coli TG1.

Randomisation of 32 and 20 bases for the pelB and g3 leaders respectively is carried out: (i) near and within the Epsilon sequence just upstream the Shine-Delgarno sequence (ii) downstream the Shine-Delgarno sequence near and within the Downstream box [50] (iii) within the leader peptide at the N-terminal region containing the positively charged amino acid residues, in the hydrophobic region [51] and in the C-terminal region close to the highly conserved peptidase cleavage site [52].

Phage is produced as described previously [25] except that the helper phage KM13 (Example 3) is used instead of VCSM13 and that 0.1 mM IPTG is added when specified to the overnight culture at 30° C. Selections for resistance to trypsin and for binding [44] is done as described earlier, except that 11 µg of anti-Taq antibody (Taqstart, Clontech) is coated overnight on immunotubes (Nunc). PCR screening is done with primers 6 and 7 using single E. coli TG1 colonies containing the phagemid as template following a previously described protocol; after gel electrophoresis on a 2% agarose gel. The size of the amplified fragment is used as a criterion to establish whether deletions within the polymerase gene have occurred.

The calculated diversity of the libraries computed from the degeneracy of the synthesised oligonucleotides is about $3.7 \times 10^{13} = 4^9 \times 3^7 \times 2^{16}$ and $1.7 \times 10^7 = 44 \times 216$ for the pelB and g3 leaders respectively. After transformation of E. coli with the phagemid libraries, the library size measured as the number of ampicillin-resistant colonies is found to be $1.3 \times 10^7$ and $9.6 \times 10^6$ for the pelB and g3 leaders respectively.

The selection for display of the polymerase is done by cleaving specifically the helper phage p3 copies with the protease trypsin so as to render non-infective all phage particles that are not expressing any p3-polymerase fusion protein.

Both libraries are mixed and the selection rounds are carried out in two conditions, with or without 0.1 mM IPTG in the culture medium. With IPTG, deletions of the polymerase gene or of part of it are noticed after round III (4 out of 28 clones) as shown by a PCR screening (see above); after round IV, these clones represent most of the population (28 out of 30). Without IPTG, these clones represent a significant part of the selected ones after round VI (3 out of 12). The selection is therefore changed from round five on by introducing in addition to selection for protease resistance, a selection for binding to an anti-Taq antibody. After the selection rounds VII and VIII, (3 out of 13) and (0 out of 19) clones respectively correspond to deleted p3-polymerase fusion proteins.

For characterisation of the leaders, the HindIII-NcoI fragments are subcloned after PCR amplification of individual E. coli colonies. The resulting phagemids are noted pHEN1-1x/Stoffel subcloning with x=7, 9, 10 and 12. The HindIII-NcoI and the NcoI-NotI fragment corresponding to the Stoffel fragment is sequenced on both strands using a 373A DNA sequencer (Applied Biosystems).

For ELISA, an anti-Taq antibody (Taqstart, Clontech) is used for coating the ELISA plate and an anti-M13-horseradish peroxidase fusion protein (Pharmacia Biotech) is used for detection in a standard protocol [44].

Expression of polymerase in the supernatant is made by infection of E. coli HB2151 with selected phagemids [25, 27] except that the IPTG concentration is 0.1 mM instead of 1 mM. About 10 µl of supernatant is loaded on a polyacrylamide gel for electrophoresis (Novex); the gel is blotted onto nitrocellulose (Protran, Schleicher and Schuell) and an anti-Taq polymerase antibody (Taqstart, Clontech), and a goat anti-mouse IgG-horseradish peroxidase (Sigma) prior to detection on autoradiography films by chemiluminescence (ECL™ chemiluminescence reagents, Amersham).

Four individual clones 7, 9, 10 and 12 from round VII, that were screened for protease resistance among 12 clones, are further characterised. To ensure that only mutations within the signal sequence are considered, and not mutations somewhere else within the phagemid that may have occurred during amplification at the various rounds, the signal sequences are subcloned into the original vector. The results shown in Table 5 indicate that optimal polymerase display for the selected clone 10 is about 50 fold higher than for the original sequence. This result is confirmed independently within experimental errors by an ELISA using anti-Taq antibody and anti-M13-HRP: $10^9$ phage particles of the pelB leader phagemid pHEN1-Stoffel (signal to noise ratio: 1.46) give an identical signal as $10^7$ phage particles of clone 10 (signal to noise ratio: 1.47).

The expression of Stoffel fragment in E. coli HB2151 is also studied for the various leaders (see Table 6). The concentration of Stoffel fragment in the culture supernatant is estimated by comparing the spot intensities for known amounts of polymerase and found to be about 0.1 mg/l for the pelB leader. A 3-fold increase in expression is observed for the leaders 17 and 110, whereas an about 3-fold decrease is noted for leader 19.

Table 5. Number of Phage-Polymerases Per Phage Particle with Leader pelB, as a Function of Temperature and IPTG Concentrations.

The phage titer is measured as the number of infective phage particles and the phage-polymerase titer as the number of infective phage particles after treatment with trypsin. The number of phage-polymerases per phage particle is the ratio of the titers. As the phage particles were rescued with a helper phage, phage displays either a p3-polymerase fusion protein and a few p3 copies containing a trypsin-cleavage site or only these p3 copies.

TABLE 6

| Phage characterisation for leader pelB or selected leaders from round VII for optimal polymerase display | | | |
|---|---|---|---|
| Temperature | 25° C. | 30° C. | 37° C. |
| 0 mM IPTG | $1.7 \times 10^{-3}$ | $9.1 \times 10^{-4}$ | $1.2 \times 10^{-3}$ |
| 0.1 mM IPTG | $9.1 \times 10^{-3}$ * | $8.3 \times 10^{-3}$ | $2.4 \times 10^{-3}$ * |
| 1 mM IPTG | $1.5 \times 10^{-2}$ * | $5.5 \times 10^{-3}$ * | $1.2 \times 10^{-3}$ * |

(same legend as for Table 5; culture in 2xTY at T = 30° C. without IPTG).
* in these conditions, the phage titer drops below 1010/ml of culture medium.

TABLE 7

| Randomised and selected sequences. | | |
|---|---|---|
| Leader | Titer × $10^{11}$ | Number of phage-polymerases per phage particle |
| pelB | 1.2 | $9.1 \times 10^{-4}$ |
| 17 | 2.0 | $2.5 \times 10^{-2}$ |
| 19 | 0.5 | $8.3 \times 10^{-3}$ |
| 110 | 0.7 | $4.3 \times 10^{-2}$ |
| 112 | 1.6 | $1.4 \times 10^{-2}$ |

The randomised DNA sequence is given from 5' to 3'; above and below it, the bases that differ from the given sequence in the signal sequences pelB, 17, 19, 110 and 112 are indicated. The Shine-Delgamo sequence, the start codon and the last codon of the signal sequence, GCC, have been underlined. The HindIII and the NcoI restriction sites are in italics. The corresponding amino acid sequences are given below. Library I is initially designed from the pelB leader and library II from the g3 leader.

```
III-A. From library I
pelB                    AATT      A    T       AATAC              (SEQ ID NO: 25)

5' AAGCTTGCATGCANNDDCTNT DTCAAGGAGACAGTCATAATGARRNNB CT (SEQ ID NO: 26)

17                      GCAT      C    G       AGACG              (SEQ ID NO: 27)

110                     CGGG      G    T       GAGGG              (SEQ ID NO: 28)

112                     CCAG      C    T       GGCGG              (SEQ ID NO: 29)

pelB        CCT CGGC GCCGCT GA    GCGGC CAG    C    G             (SEQ ID NO: 30)

ATTGSYAAYRSYASYASYAGBNTTGTTATTACTC  SYANY CVNNCYGDCCATGGCC 3' (SEQ ID NO: 31)

17          GC  TGGT   CT   GT    GA  CC  CC   GGT C    T         (SEQ ID NO: 32)

110         GC  TGCT   GT   GC    GG  CC  AT   GCG C    G         (SEQ ID NO: 33)

112         GT  TAGC   GC   GT    GG  CT  GC   CCC C    A         (SEQ ID NO: 34)

pelB        M K Y L L P T A A A G L L L L A A Q P A M A            (SEQ ID NO: 35)

17            K T   A M V L V G       P P G P S                    (SEQ ID NO: 36)

110           R G   A M L V A G       P I   A P A                  (SEQ ID NO: 37)

112           R R   V   I     A A V G     L A P P T                (SEQ ID NO: 38)

III-B. From library II
g3 leader             GAGC    TT G A A                             (SEQ ID NO: 39)

5' AAGCTTTGNNNNNCTTTTTTWWGGAGATTTTCAACRTGARAARATTATTAT  (SEQ ID NO: 40)

19                    GGGC    TA  A G G                            (SEQ ID NO: 41)

GC    CC    GT CC    A    C C                        (SEQ ID NO: 42)

TCSYAATTSYTTTAGTTSYTSYTTTCTWTGYGGYCCAGCCGGCCATGG CC3'   (SEQ ID NO: 43)

19            CT    CC    GT GC    A    T T                        (SEQ ID NO: 44)

g3 leader       M K K L L F A I P L V V P F Y A A Q P A M A        (SEQ ID NO: 45)

19                R R     L P         V A     Y V V                (SEQ ID NO: 46)
```

Example 8

Selection of a Catalytic Activity Using Protease-Cleavable Helper Phage

A strategy for the selection of catalysts by phage display is based on selection of the reaction product of a catalytic reaction, and the use of proximity effects to select the catalyst. In this strategy, a tagged substrate is crosslinked to the phage in the proximity of the displayed enzyme; the phage is thereby attached to a solid-phase and released by an intramolecular cleavage reaction catalysed by the displayed enzyme [53].

A similar approach has been applied to the selection of active DNA polymerase variants. The approach involves two chemically independent reactions, the catalytic reaction leading to a product (in this case distinguished by incorporation of a biotin tag) and a chemical crosslinking reaction by which the substrate (and product) are linked to the phage. Selection of the phage by streptavidin beads therefore selects for phages which are chemically attached to tagged product; these reactions are more likely to be coupled on the same phage as reactions in cis are favoured over reactions in trans by proximity.

Maleimides are used in a chemical cross-linking reaction. These are known to react with thiols and in alkaline solutions with amino groups, and are therefore capable of reacting with a wide range of sites on the phage and on the displayed enzyme. A covalent product between the major coat protein (p8) and N-biotinoyl-N'-(6-maleimidohexanoyl) hydrazide, is detected by SELDI mass spectrometry. Two amino groups (the N-terminal Ala-1 and the residue Lys-8) are thought to be involved.

The strategy is tested using DNA polymerases in view of their central role in molecular evolution. A maleimidyl group is introduced at the 5' end of a DNA primer; the product is tagged by addition of biotinylated dUTP to the 3' end of the primer by the catalytic action of the polymerase. The Klenow and Stoffel fragments of DNA polymerase I *Escherichia coli* and *Thermus aquaticus*, respectively, are cloned for display by fusion to the pIII coat protein of filamentous bacteriophage by conventional techniques. Both fragments lack the 5' to 3' exonuclease domains; the Stoffel fragment also lacks a 3' to 5' exonuclease activity.

The fusion protein is cloned on a phagemid (pHEN1) [25], and is rescued by a helper phage. The polymerase fragments are shown to be displayed on the phage (after rescue with helper phage) by binding of the phage to wells coated with anti-polymerase antibodies as detected by ELISA (not shown). The phage are also analysed by Western blot using anti-p3 or anti-polymerase antibodies. This confirms the presence of the fusion protein, but also indicates contamination by free polymerase. Presumably this arises by secretion from the bacterial host through incomplete suppression of the amber stop codon or by cleavage from the phage surface. This is removed by a further step of ultracentrifugation or by size exclusion chromatography. The purified phages are assayed for DNA polymerase activity in a primer/template extension assay with radioactively labelled $\alpha^{32}P$-dCTP and found to be active.

However as is indicated by the Western blots, the polymerase-p3 fusion protein is poorly incorporated into the phage compared to the p3 protein. This appears to be due to incorporation of p3 from the helper phage, as shown by the alternative use of a helper phage (KM13) in which the p3 protein of the helper phage (but not that of fusion protein) can be cleaved with trypsin so as to render it incapable of mediating infection (Examples 3 and 4). Thus after proteolysis only those phages that had incorporated the fusion protein are infective; from the loss in titre after proteolysis we estimate that only one phage particle in a thousand had incorporated the fusion protein. The selection process, relying on tagging by polymerase in cis, would be compromised by such a great excess of phages lacking the polymerase but available for tagging in trans. Selected phages are therefore treated with trypsin to destroy the infectivity of those lacking the displayed polymerase.

The phage displaying the Stoffel fragment are incubated with primer 13 [TTT CGC AAG ATG TGG CGT] (SEQ ID NO: 47) comprising a 5' maleimidyl group and a 3' biotinylated nucleotide. After incubation the phage are captured on streptavidin-coated beads, with a yield of about 1-5% of infectious phage. This shows that primer can be chemically cross-linked to the phage, presumably via p8 protein as shown for the N-biotinoyl-N'-(6-maleimidohexanoyl) hydrazide. The phage are then incubated with primer 1b [GCGAAGAT-GTGG] (SEQ ID NO: 48) comprising a 5' maleimidyl group in the presence of biotin-dUTP 2 and template 3 [AAA TAC AAC AAT AAA ACG CCA CAT CTT GCG] (SEQ ID NO: 49). Capture of the phage is dependent on presence of 1b, 2 and 3 (Table 8), but also on the inclusion of trypsin, which cleaves the helper phage to reduce non-specific phage isolation.

TABLE 8

Selection of catalytically active phage-Stoffel particles.

| $\phi i^{[a]}$ in tu | $\phi f$ In tue | Yield In % | Conditions[c] |
|---|---|---|---|
| $8.4 \times 10^5$ | $2.0 \times 10^4$ | 2.4 | |
| $3.6 \times 10^5$ | $1.0 \times 10^2$ | 0.028 | primer 1b |
| $4.4 \times 10^5$ | $3.0 \times 10^2$ | 0.068 | biotinylated dUTP 2 |
| $4.8 \times 10^5$ | $3.0 \times 10^2$ | 0.062 | template 3 |
| $4.4 \times 10^9$ | $4.0 \times 10^6$ | 0.091 | trypsin |
| $1.5 \times 10^9$ | $5.5 \times 10^5$ | 0.037 | trypsin, primer 1b |

$\phi i$ and $\phi f$ denote the number of transformation units (tu) prior
[a]and after
[b]the selection.
Yield = $\phi f/\phi i$.
[c]+ primer 1b, + biotinylated dUTP 2, + template 3 and + trypsin.

Example 9

Selection for Disulphide-Containing Polypeptides

For the cloning of (poly)-peptide encoding DNA fragments and their display for selection between barnase and p3, the phage fd-3 is constructed (FIG. 5). Phage fd-3 comprises the H102A mutant of barnase N-terminally fused to the p3 gene of phage fd-TET. Between the codon for the last residue of barnase and the first residue of p3 is the nucleotide sequence CTG CAG GCG GTG CGG CCG CA (SEQ ID NO: 50). This sequence contains a PstI DNA restriction site (in italics) for insertion of DNA fragments flanked by PstI restriction sites. The sequence further introduces a frame shift between barnase and p3, which prevents expression of the correct p3 reading frame in fd-3. Phage particles of phage fd-3 therefore do not display the infection protein p3 and are non-infectious.

Phage fd-3 is therefore well suited as a cloning vector as vectors without PstI DNA inserts after ligation are not propagated during selection. Statistically 1 out of 3 random DNA inserts in the PstI restriction site will (except for the presence of stop-codons within the insert) create an open reading frame spanning barnase, the insert itself and p3 and result in infectious phage particles containing p3 in the phage coat. In these recombinant clones barnase is followed by the insert, which is then followed by the amino acid residues AGGAAA (SEQ ID NO: 80) before the start of the p3 protein. This AGGAAA (SEQ ID NO: 80) peptide should provide enough flexibility in the fusion protein to enable the infectivity function of p3 and the access of the protease to the N-terminal appendices of p3.

Genomic DNA from the *E. coli* strain TG1 is amplified in 30 cycles of a polymerase chain reaction (PCR) with an annealing temperature of 48° C. using the oligonucleotide SN6MIX (5'-GAG CCT GCA GAG CTC AGG NNN NNN-3') (SEQ ID NO: 51), which comprises 6 degenerate positions at the extendible 3' end to ensure random priming. In a second step of 30 PCR cycles with an annealing temperature of 52° C. primary PCR products are extended by re-amplification with the oligonucleotide XTND (5'-CGT GCG AGC CTG CAG AGC TCA GG-3') (SEQ ID NO: 52). Products with a length of around 150 bp from this reaction are purified from an agarose gel and reamplified in 30 PCR cycles using an annealing temperature of 52° C. and the oligonucleotide XTND. These reamplified 150 bp fragments are partially digested with SacI (site indicated in bold in the oligonucleotides) and ligated for dimerisation. Ligated products are reamplified in a further 10 PCR cycles with an annealing temperature of 44° C. followed by a 30 PCR cycles with an annealing temperature of 55° C. using the oligonucleotide XTND. The annealing temperatures are chosen to discriminate against priming of the oligonucleotide in the middle of the dimerised fragments. The reaction product is size purified twice on an agarose gel to remove monomers and oligomers (non-dimers).

The final dimer fraction is amplified by PCR using an annealing temperature of 55° C. and the oligonucleotide XTND on a large scale, digested with PstI (site indicated in italics in oligonucleotides) and ligated into the also PstI digested and phosphatased vector fd-3. After electroporation into *E. coli* bacteria a repertoire of $3.6 \times 10^7$ recombinants is obtained. Sequence analysis of randomly picked clones reveal the presence of mainly dimeric (11 out of 14) and some monomeric (2 out of 14) DNA inserts.

Reinfection of *E. coli* bacteria with phage produced from the initial population of transformed cells yields, according to sequence analysis of twenty randomly picked clones, a library of infectious phages containing almost exclusively barnase-(in-frame, no-stop-dimer-insert)-p3 fusions. Non-infectious phages arising from vector without insert and from vector with out-of-frame or stop-codon containing inserts are not propagated in the infection step. The vector fd-3 is therefore suitable to create a repertoire of polypeptides randomly generated through dimerisation of DNA fragments from the *E. coli* genome.

This repertoire of polypeptides displayed as an inserted fusion between barnase and p3 on phage fd is subjected to proteolytic digestion with trypsin and thermolysin alone or a mixture of both (1 ng/µl each) in TBS-Ca buffer (25 mM Tris, 137 mM NaCl, 1 mM $CaCl_2$, pH 7.4). After proteolysis phage is captured with biotinylated barstar bound to a Streptavidin coated microtitre well plate and eluted at pH 2.0. Phage is neutralised to pH 7 and propagated through reinfection of the *E. coli* cells and selected for a second round as before. All steps are performed in the absence of any reducing agent like dithiothreitol (DTT) or β-mercaptoethanol, which would reduce and thereby cleave any potential disulphide bonds formed between cysteine sidechains within selected polypeptides.

Randomly picked phages, which are eluted after the first and second round of proteolytic selection, are analysed for binding to barstar after incubation with a mixture of trypsin and thermolysin under the conditions of the selection (Table 9). Their sequence is determined (Table 9). 17 out of 18 analysed clones treated with a mixture of trypsin and thermolysin during selection are found to bind biotinylated barstar after incubation with trypsin and thermolysin. 5 out of 8 analysed clones treated with trypsin during selection bound biotinylated barstar after incubation with trypsin and thermolysin, whilst 9 of 14 analysed clones treated with thermolysin are found to bind. No randomly picked clones not treated with a protease during selection bind biotinylated barstar after incubation with trypsin and thermolysin. Binding to biotinylated barstar shows that the polypeptide insertion between barnase and p3 on the phage retains its overall covalent integrity and therefore keeps the N-terminal tag (barnase) and the infection protein p3 (and thereby the phage particle as a whole) covalently linked.

However, the possibility of proteolytic digestion of the peptide backbone can not be excluded, as the inserts may also be kept covalently linked through bonds between sidechain groups like the $SH_2$ groups of cysteines. Sequence analysis of the selected clones reveal that 19 of 25 (76%) resistant clones contain two or more cysteine residues.

To analyse the role of possible disulphide bonds in the polypeptide inserts, 13 of the selected phages are analysed for binding to biotinylated barstar (and thereby for a covalent linkage of barnase and p3 through the insert) after treatment with trypsin and thermolysin followed by a wash with 20 mM DTT before detection of bound phage. 2 phage clones, which bind barstar after protease treatment without DTT wash and contain no cysteines, are unaffected by the DTT treatment. Another 2 phage clones, which bind barstar after protease treatment without DTT and contain two or more cysteines, are also observed to bind barstar after protease and DTT treatment. This suggests that their inserts are protected from proteolysis of their peptide backbone despite the presence of principle substrate sites for the proteases.

These inserts are therefore protected from proteolytic attack due to a conformational restraint of their peptide backbone. However, 9 phage clones which bind barstar after protease treatment without DTT wash and contain two or more cysteines are observed not to bind barstar after protease and DTT treatment. This suggests that their inserts are proteolytically cleaved in their peptide backbone, but are held together by disulphide bonds between cysteine sidechains in the absence of the reducing agent DTT. These inserts are therefore not protected from proteolytic attack due to a conformational restraint of their peptide backbone.

Thus, the method of the present invention may be configured to select for cysteine-containing polypeptides, even where the polypeptides would by susceptible to protease attack since the polypeptides are capable of being held together in the selection step by disulphide bonds.

Table 9. Barstar Binding of Phages Displaying Barnase-p3 Fusion Inserts Selected after Proteolytic Treatment Under Non-Reducing Conditions and Amino Acid Sequences of their PstI Inserts in Vector Fd-3.

Barstar binding (−DTT) after proteolysis of phage with trypsin and thermolysin (2 ng/µl each) without a 20 mM DTT wash is determined by measurement of a signal that is at least 60% of the signal for barstar binding of phage without protease treatment. Barstar binding (+DTT) after a 20 mM wash is determined by measurement of a signal that is at least 60% of the signal for barstar binding (−DTT) without a 20 mM DTT wash. Phage are randomly picked after one (1×) or two (2×) rounds of proteolysis with trypsin (Tr) or thermolysin (Th). Phages are treated with proteases, captured with biotinylated barstar microtitre well plates, and washed with 20 mM DTT where applicable. Bound phage are detected with a horse radish peroxidase conjugated anti-M13 phage antibody (Pharmacia Biotech).

| Phage clone | Proteo-lytic selec-tion | Barstarbindg -DTT | +DTT | Amino acid sequence of inserts |
|---|---|---|---|---|
| TA-1.2 | 1xTr | yes | no | LQSSGDCVIS DTCIAGMAEA AACEEKFSSQ NVGLTITVTP CLSSA (SEQ ID NO: 53) |
| TA-2.25 | 2xTr | yes | no | LQSSGCGSSG SSINCLPCGA TSRGTSPLAS GLPSSATIHC LSSA (SEQ ID NO: 54) |
| TA-2.26 | 2xTr | yes | no | LQSSGDSAGC KNMTGGRLYA HTLEAIIPGF AVSAPACEPA (SEQ ID NO: 55) |
| TA-2.27 | 2xTr | yes | yes | LQSSGCVRLK RTSVNHQPDA WPEPHLKAAC EPA (SEQ ID NO: 56) |
| TA-2.30 | 2xTr | yes | no | LQSSGCGSSG SSINCLPCGA TSRGTSPLAS GLPSSATVQC LSSA (SEQ ID NO: 57) |
| TB-1.10 | 1xTh | yes | yes | LQSSGKIVQA GANIQDGCIM HGYCDTDTIV GENGHIGLSS A (SEQ ID NO: 58) |
| TB-1.11 | 1xTh | yes | yes | no insert, Barnase & p3 in frame |
| TB-2.33 | 2xTh | yes | no | LQSSGVCVIS DTCIAGTAEA AACEEKFSSQ NVGHTITETP CLSSA (SEQ ID NO: 59) |
| TB-2.34 | 2xTh | yes | no | LQSSGCGSSG SSINCLPCGA TSRGTSPLAS GLPSSATIQC LSSA (SEQ ID NO: 60) |
| TB-2.35 | 2xTh | yes | no | LQSSGQDSQR EHASHTAEDD CEDQTRIHQH IREVDFVDTP QEVDDCRAAL SSA (SEQ ID NO: 61) |
| TB-2.37 | 2xTh | yes | no | LQSSGCVRLK RTSVNHQPDA WPEPHLKAAC EPA (SEQ ID NO: 62) |
| TB-2.38 | 2xTh | yes | yes | LQSSGVRPA (SEQ ID NO: 63) |
| TB-2.39 | 2xTh | yes | no | LQSSGCGSS GSSINCLPCGA TSRGTSPLAS GLPSSATIQ CLSSA (SEQ ID NO: 64) |

Example 10

Use of Reducing Agents to Eliminate Disulphide-Related Background

The repertoire of polypeptides described in Example 9 is digested as before with both trypsin and thermolysin (Example 9) except for an additional washing step here with 50 mM DTT after binding of the proteolytically treated phage to the microtitre well plates coated with Streptavidin-biotinylated barstar. This washing step is designed to wash off phage displaying an N-terminal barnase tag, which is no longer linked to p3 through an intact polypeptide backbone but only through disulphide bonds between cysteine sidechains in the polypeptide inserts between the barnase tag and p3.

12 randomly picked phages eluted after the second round of proteolysis are analysed for stability against a mixture of trypsin and thermolysin under the conditions of the selection and their sequence is determined (Table 10). 10 clones treated with a mixture of trypsin and thermolysin during selection bind biotinylated barstar after incubation with trypsin and thermolysin followed by washing with 50 mM DTT before detection of captured phage. Only one of these clones contain two or more cysteines.

Proteolytic treatment of the phage library followed by a wash with DTT therefore allows the selection of peptide inserts which are protected from proteolysis and which are not held together through disulphide bonds.

Table 10. Barstar Binding of Phages Displaying Barnase-p3 Fusion Inserts Selected after Proteolytic Treatment Followed by Treatment with 50 mM DTT and Amino Acid Sequences of their PstI Inserts in Fd-3.

Barstar binding (+DTT) after proteolysis of phage with trypsin and thermolysin (2 ng/µl each) followed by a 50 mM DTT is determined by measurement of a signal for Barstar binding (+DTT), which is at least 60% of the signal for barstar binding of phage without protease treatment. Phage are randomly picked after two (2×) rounds of proteolytic with trypsin (Tr) and/or thermolysin (Th). Phages are treated with proteases, captured with biotinylated barstar in microtitre well plates, and washed with 50 mM DTT where applicable. Bound phage is detected with a horse radish peroxidase conjugated anti-M13 phage antibody.

| Phage Clone | Proteo-lytic selec-tion | Barstarbindg +DTT | Amino acid sequence of inserts |
|---|---|---|---|
| B2-13 | 2xTr/Th | yes | LQSSGTEVDR GNQQHDTNDR DFTHTPLSS A (SEQ ID NO: 65) |
| B2-14 | 2xTr/Th | yes | LQSSGSVAQG SSASVDVTAT NAVLSADSL SLGGGEPA (SEQ ID NO: 66) |
| B2-22 | 2xTr/Th | yes | LQSSGGAVAV TPGPVLSSA (SEQ ID NO: 67) |
| B2-23 | 2xTr/Th | yes | LQSSGHCRGK PVLCTHTA (SEQ ID NO: 68) |
| B2-15 | 2xTr/Th | yes | LQSSGVRPA (SEQ ID NO: 69) |
| B2-17 | 2xTr/Th | yes | no insert, Barnase & p3 in frame |
| B2-20,21 | 2xTr/Th | yes | no insert, Barnase & p3 in frame |
| B2-16,24 | 2xTr/Th | yes | LQSSGEPAPA HEAKPTEAPV AKAEAKPETP AHLSSA (SEQ ID NO: 70) |
| B2-18 | 2xTr/Th | no | LQSSGCVRLK RTSVNHQPDA WPEPHLKAAC EPA (SEQ ID NO: 71) |

-continued

| Phage Clone | Proteolytic selection | Barstarbindg +DTT | Amino acid sequence of inserts |
|---|---|---|---|
| B2-19 | 2xTr/Th | no | LQSSGVVDWA KMREIADSIG AYLFVDMAHV AALSSA (SEQ ID NO: 72) |

REFERENCES

Figure 1:
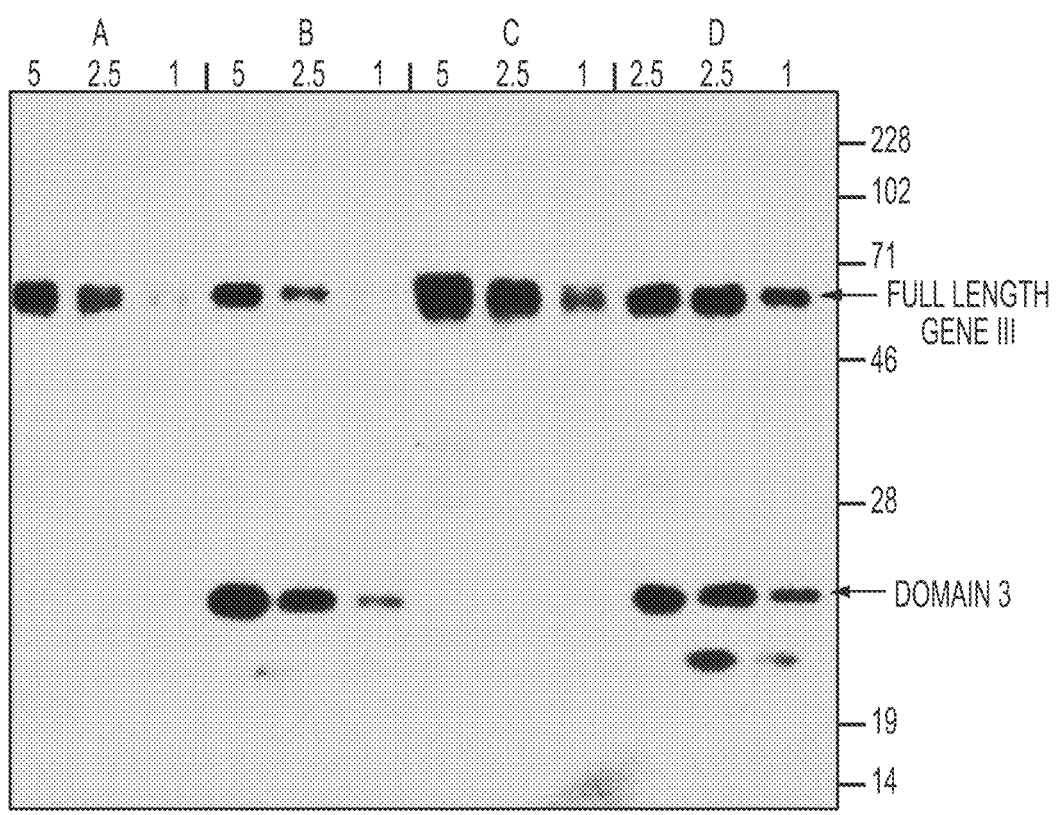
FIG. 1. Cleavage of phages with protease sites. Phages were prepared by rescue with KM13 (pHEN1, A+B), or with VCSM13 (pK1, C+D). Uncleaved (A+C) or cleaved with trypsin (B+D). 5 µl 2.5 µl and 1 µl phages were loaded as indicated. Molecular weight markers are in kD.
Figure 2:
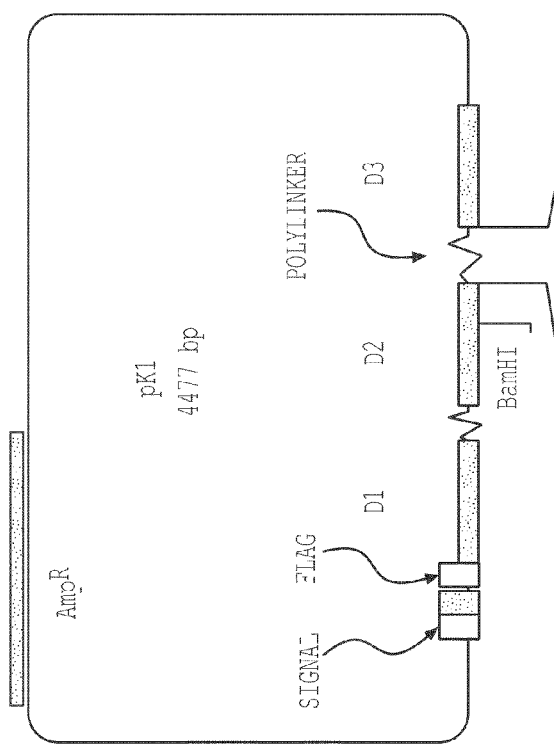
FIG. 2. The phagemid vectors pK1 and pK2. These vectors contain a protease cleavable sequence between D2 and D3 of the phage p3 protein. In pK1 (SEQ ID NO: 73 and SEQ ID NO: 74, respectively), D2+D3 are in frame; in pK2 (SEQ ID NO: 75 and SEQ ID NO: 76, respectively), D3 is out of frame.
Figure 3:
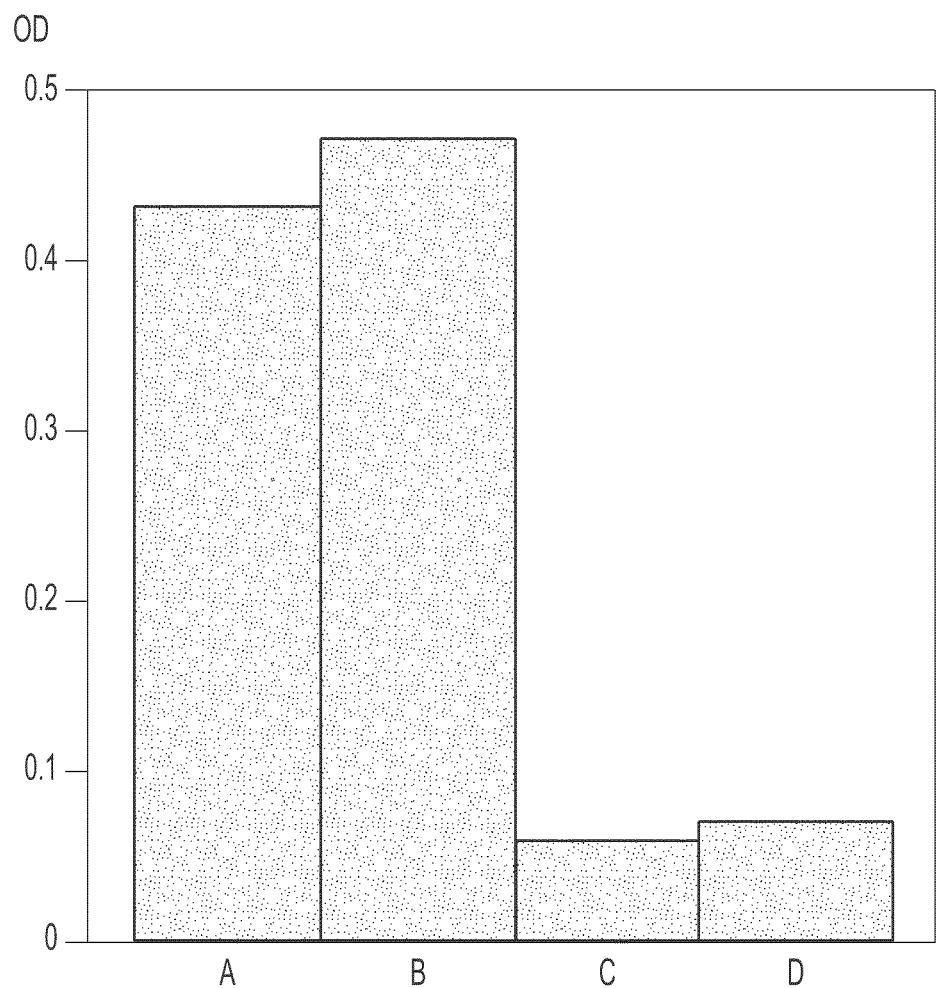
FIG. 3. Binding of phage-barnase to barstar. Phage displaying different fusion protein are incubated with biotinoylated barstar captured on streptavidin-coated plate and detected by ELISA. a) barnase mutant A, b) barnase mutant B, c) villin, d) no phage.
Figure 4:
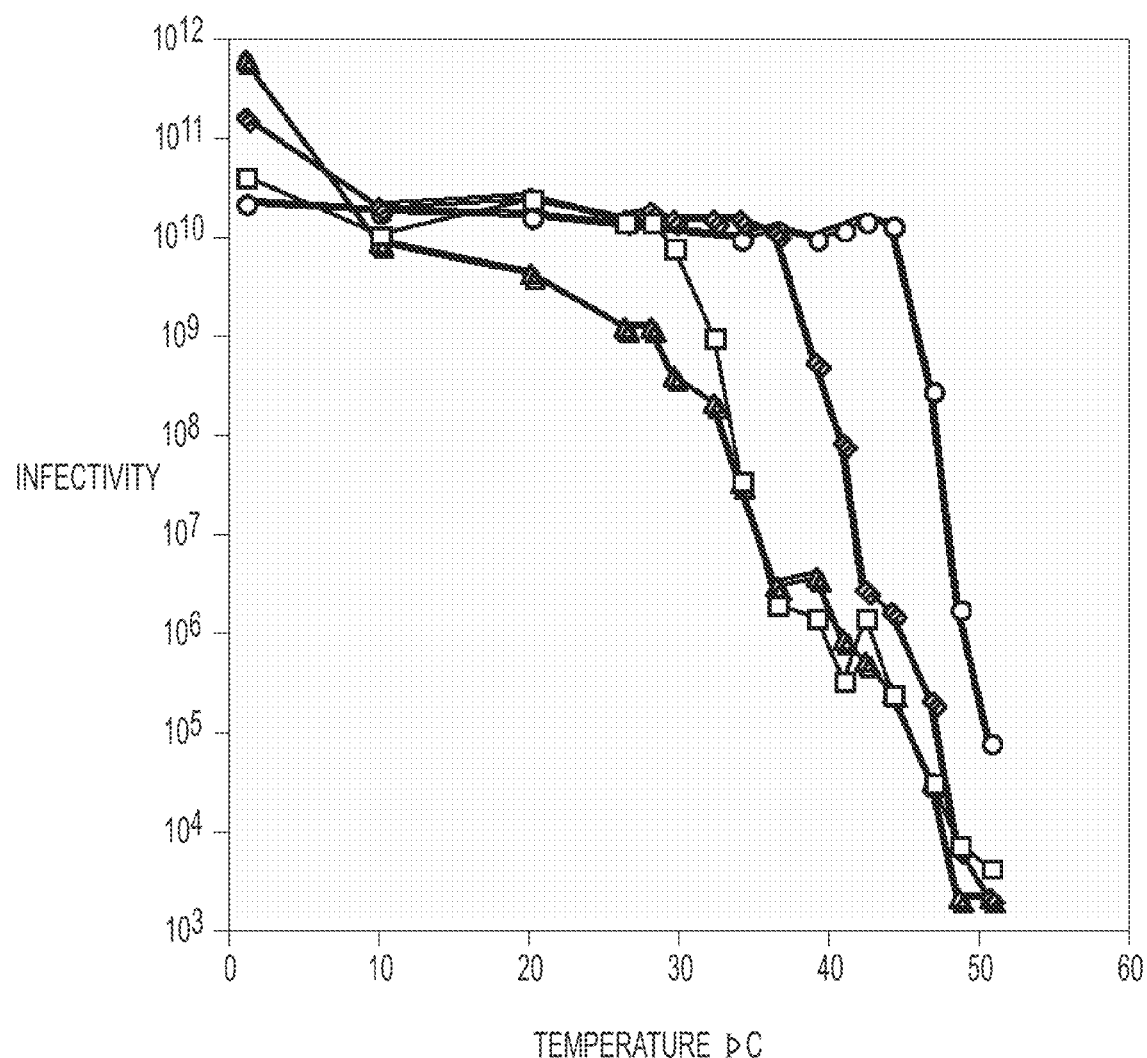
FIG. 4. Temperature denaturation of phage fusion proteins. Phagemids were rescued with KM13, infectivity (TU/rnl) shown after incubation and cleavage with trypsin at given temperatures. Fusion with villin subdomain (triangles), barnase mutant A (diamonds), barnase mutant B (squares), pHEN1-chloramphenicol resistant (circles).
Figure 5:
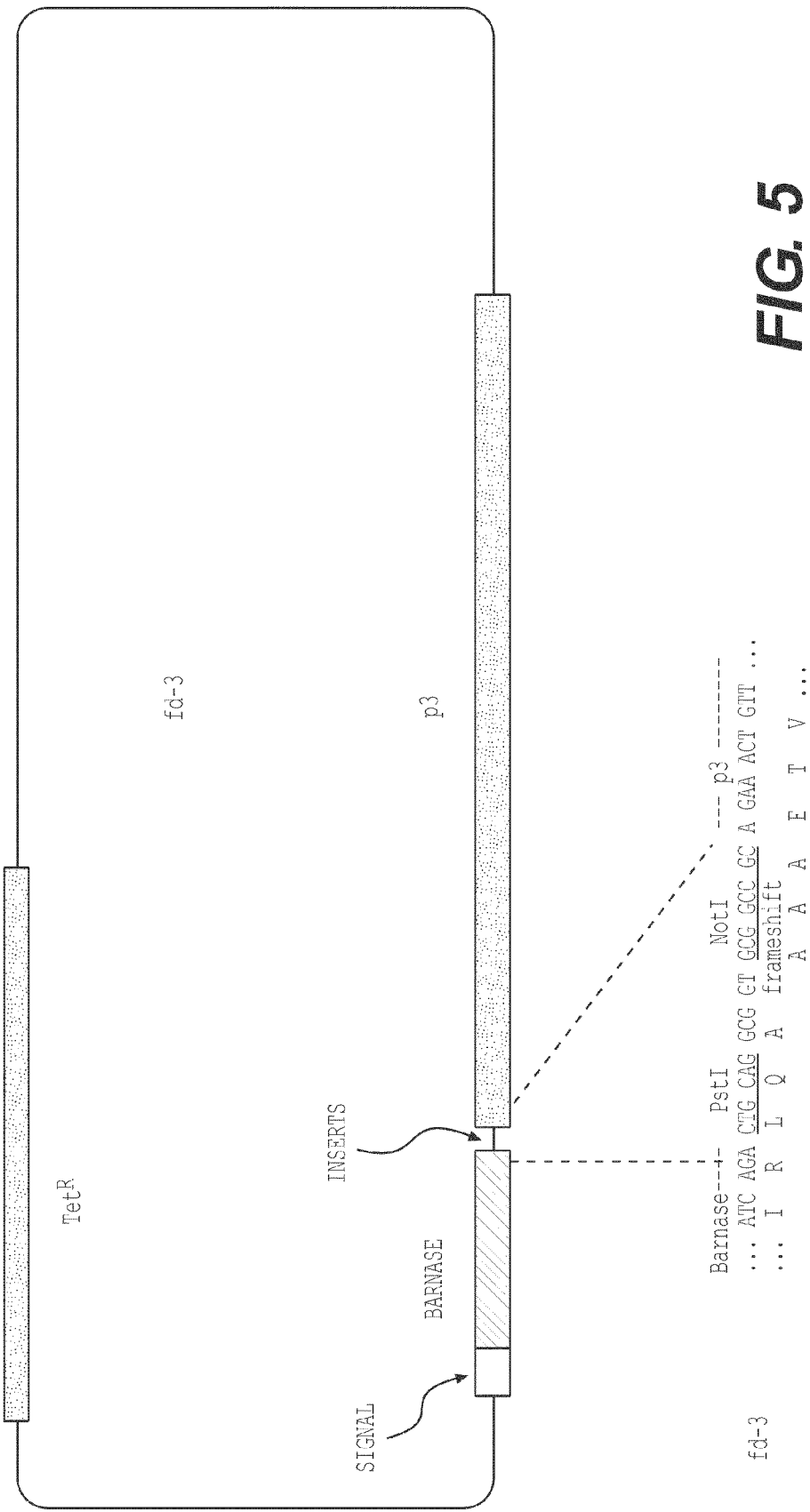
FIG. 5. The fd vector fd-3. The gene for the H102A mutant of Barnase is introduced by subcloning into fd-DOG [43] after PCR amplification with suitable oligonucleotides using the restriction sites ApaLI (at the Barnase 5' end) and NotI to create fd-3. The nucleotide and amino acid sequence of the junction between Barnase and p3 sequences is shown in expanded view (SEQ ID NO: 77 and SEQ ID NO: 78, respectively).
Figure 6:
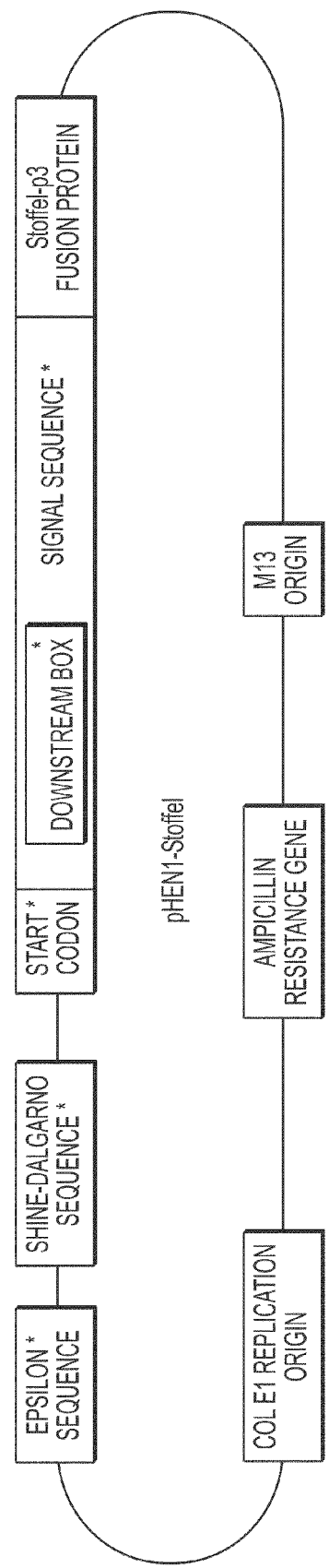
FIG. 6. Map of phagemid vector used for display of Stoffel fragment on the surface of phage. The asterisk shows sequences that are randomised at least partially in libraries I and II.

1. Rubingh, D. N. (1997). Protein engineering from a bioindustrial point of view. *Current Opinion in Biotechnology.* 8, 417-422.
2. Fersht, A. R. (1993). Protein folding and stability: the pathway of folding of barnase. *FEBS Letters.* 325, 5-16.
3. Zhao, H., et al. (1998). Molecular evolution by staggered extension process (StEP) in vitro recombination. *Nature Biotechnology.* 16, 258-261.
4. Patten, P. A., R. J. Howard, and W. P. C. Stemmer. (1997). Applications of DNA shuffling to pharmaceuticals and vaccines. *Current Opinion in Biotechnology.* 8, 724-733.
5. Sauer, R. T. (1996). Protein folding from a combinatorial perspective. *Folding & Design.* 1, R27-R30.
6. Munson, M., et al. (1996). What makes a protein a protein? Hydrophobic core designs that specify stability and structural properties. *Protein Science.* 5, 1584-1593.
7. Dahiyat, B. I., C. A. Sarisky, and S. L. Mayo. (1997). De Novo Protein Design: Towards Fully Automated Sequence Selection. *Journal of Molecular Biology.* 273, 789-796.
8. Riddle, D. S., et al. (1997). Functional rapidly folding proteins from simplified amino acid sequences. *Nature Structural Biology.* 4(10), 805-809.
9. Hoogenboom, H. R. and G. Winter. (1992). By-passing Immunisation. Human Antibodies from Synthetic Repertoires of Germline VH Gene Segments Rearranged in Vitro. *Journal of Molecular Biology.* 227, 381-388.
10. Winter, G., et al. (1994). Making Antibodies by Phage Display Technology. *Annual Review of Immunology.* 12, 433-455.
11. Braisted, A. C. and J. A. Wells. (1996). Minimizing a binding domain from protein A. *Proc. Natl. Acad. Sci. USA.* 93, 5688-5692.
12. O'Neil, K. T., et al. (1995). Thermodynamic Genetics of the Folding of the B1 Immunoglobulin-Binding Domain From Streptococcal Protein G. *Proteins: Structure, Function, and Genetics.* 21, 11-21.
13. Gu, H., et al. (1995). A phage display system for studying the sequence determinants of protein folding. *Protein Science.* 4, 1108-1117.
14. Hubbard, S. J., F. Eisenmenger, and J. M. Thornton. (1994). Modeling studies of the change in conformation required for cleavage of limited proteolytic sites. *Protein Science.* 3, 757-768.
15. Fontana, A., et al. (1997). Probing the partly folded states of proteins by limited proteolysis. *Folding & Design.* 2, R17-R26.
16. Kamtekar, S., et al. (1993). Protein Design by Binary Patterning of Polar and Nonpolar Amino Acids. *Science.* 262, 1680-1685.
17. Davidson, A. R. and R. T. Sauer. (1994). Folded proteins occur frequently in libraries of random amino acid sequences. *Proc. Natl. Acad. Sci. USA.* 91, 2146-2150.
18. Davidson, A. R., K. J. Lumb, and R. T. Sauer. (1995). Cooperatively folded proteins in random sequence libraries. *Nature Structural Biology.* 2(10), 856-864.
19. Matthews, D. J. and J. A. Wells. (1993). Substrate Phage: Selection of Protease Substrates by Monovalent Phage Display. *Science.* 260, 1113-1117.
20. Riechmann, L. and P. Holliger. (1997). The C-Terminal Domain of To1A Is the Coreceptor for Filamentous Phage Infection of *E. coli. Cell.* 90, 351-360.
21. Smith, G. P. (1985). Filamentous Fusion Phage: Novel Expression Vectors That Display Cloned Antigens on the Virion Surface. *Science.* 228, 1315-1317.
22. Krebber, C., et al. (1997). Selectively-infective Phage (SIP): A Mechanistic Dissection of a Novel in vivo Selection for Protein-ligand Interactions. *Journal of Molecular Biology.* 268, 607-618.
23. Stengele, I., et al. (1990). Dissection of Functional Domains in Phage fd Adsorption Protein. Discrimination between Attachment and Penetration. *Journal of Molecular Biology.* 212, 143-149.
24. Gray, C. W., R. S. Brown, and D. A. Marvin. (1981). Adsorption complex of Filamentous fd virus. *Journal of Molecular Biology.* 146, 621-627.
25. Hoogenboom, H. R., et al. (1991). Multi-subunit proteins on the surface of filamentous phage: methodologies for displaying antibody (Fab) heavy and light chains. *Nucleic Acids Research.* 19, 4133-4137.
26. Bass, S., R. Greene, and J. A. Wells. (1990). Hormone Phage: An Enrichment Method for Variant Proteins With Altered Binding Properties. *Proteins.* 8, 309-314.

27. Nissim, A., et al. (1994). Antibody fragments from a "single pot" phage display library as immunochemical reagents. *The EMBO Journal.* 13, 692-698.
28. Marzari, R., et al. (1997). Extending filamentous phage host range by the grafting of a heterologous receptor binding domain. *Gene.* 185, 27-33.
29. Mossakowska, D. E., K. Nyberg, and A. R. Fersht. (1989). Kinetic Characterisation of the Recombinant Ribonuclease from *Bacillus amyloliquefaciens* (Barnase) and Investigation of Key Residues in Catalysis by Site-Directed Mutagenesis. *Biochemistry.* 28, 3843-3850.
30. Meiering, E. M., L. Serrano, and A. R. Fersht. (1992). Effect of Active Site Residues in Barnase on Activity and Stability. *Journal of Molecular Biology.* 225, 585589.
31. Serrano, L., et al. (1992). The Folding of an Enzyme. II Substructure of Barnase and the Contribution of Different Interactions to Protein Stability. *Journal of Molecular Biology.* 224, 783-804.
32. McKnight, C. J., P. T. Matsudaira, and P. S. Kim. (1997). NMR structure of the 35-residue villin headpiece subdomain. *Nature Structural Biology.* 4(3), 180-184.
33. McKnight, C. J., et al. (1996). A Thermostable 35-Residue Subdomain within Villin Headpiece. *Journal of Molecular Biology.* 260, 126-134.
34. Xu, D. and R. Nussinov. (1997). Favorable domain size in proteins. *Folding & Design.* 3, 11-17.
35. Kippen, A. D. and A. R. Fersht. (1995). Analysis of the Mechanism of Assembly of Cleaved Barnase from Two Peptide Fragments and Its Relevance to the Folding Pathway of Uncleaved Barnase. *Biochemistry.* 34, 1464-1468.
36. Gay, G. d. P. and A. R. Fersht. (1994). Generation of a Family of Protein Fragments for Structure-Folding Studies. 1. Folding Complementation of Two Fragments of Chymotrypsin Inhibitor-2 Formed by Cleavage at Its Unique Methionine Residue. *Biochemistry.* 33, 7957-7963.
37. Wu, L. C., R. Grandori, and J. Carey. (1994). Autonomous subdomains in protein folding. *Protein Science.* 3, 369-371.
38. Kwon, W. S., N. A. D. Silva, and J. T. Kellis. (1996). Relationships between thermal stability, degradation rate and expression yield of barnase variants in the periplasm of *Escherichia coli*. *Protein Engineering.* 9(12), 1197-1202.
39. Axe, D. D., N. W. Foster, and A. R. Fersht. (1996). Active barnase variants with completely random hydrophobic cores. *Proc. Natl. Acad. Sci. USA.* 93, 5590-5594.
40. Waldburger, C. D., J. F. Schildbach, and R. T. Sauer. (1995). Are buried salt bridges important for protein stability and conformational specificity? *Nature Structural Biology.* 2(2), 122-128.
41. Roy, S., et al. (1997). A Protein Designed by Binary Patterning of Polar and Nonpolar Amino Acids Displays Native-like Properties. *Journal of the American Chemical Society.* 119, 5302-5306.
42. Gibson, T. J., *Studies on the Epstein-Barr Virus Genome.* 1984, Univ. of Cambridge, Cambridge, UK:
43. Clackson, T., et al. (1991). Making antibody fragments using phage display libraries. *Nature.* 352, 624-628.
44. McCafferty, J., et al. (1990). Phage antibodies: filamentous phage displaying antibody variable domains. *Nature.* 348, 552-554.
45. Fisch, I., et al. (1996). A strategy of exon shuffling for making large peptide repertoires displayed on filamentous bacteriophage. *Proc. Natl. Acad. Sci. USA.* 93, 7761-7766.
46. Matouschek, A., et al. (1989). Mapping the transition state and pathway of protein folding by protein engineering. *Nature.* 340, 122-126.
47. Laemmli, U. K. (1970). Cleavage of structural proteins during the assembly of the head of bacteriophage T4. *Nature.* 227, 680-685.
48. Schatz, G. and Dobberstein, B. (1996) Common principles of protein translocation across membranes. *Science.* 271, 1519-1526.
49. Von Heijne, G. (1998) Life and death of a signal peptide. *Nature.* 396, 111-113.
50. Sprengart, M. L., Fuchs, E. and Porter, A. G. (1996) The downstream box: an efficient and independent translation initiation signal in *E. coli. EMBO J.* 15, 665-674.
51. Perlman, D. and Halvorson, H. O. (1983) A putative signal peptidase recognition site and sequence in eukaryotic and prokaryotic signal peptides. *J. Mol. Biol.* 167, 391-409.
52. Von Heijne, G. (1983) Patterns of amino acids near signal-sequence cleavage sites. *Eur. J. Biochem.* 133, 17-21.
53. Pedersen, H., Hölder, S., Sutherlin, D. P., Schwitter, U., King, D. S., Schultz, P. G. (1998) *Proc. Natl. Acad. Sci. USA.* 95, 10523-10528.

We claim:

1. A method for helper phage rescue of a phagemid comprising a fusion polypeptide to form progeny phage, wherein:
   (a) the helper phage encodes a viral coat protein comprising a protease-sensitive cleavage site;
   wherein the helper phage is a filamentous bacteriophage M13, fd or related species;
   wherein the viral coat protein is encoded by gene 3 of the filamentous bacteriophage M13, fd or related species; and
   wherein the protease-sensitive cleavage site is introduced between the second and third domain of the gene 3 protein;
   (b) the phagemid encoding a fusion polypeptide;
   wherein the sequence encoding the fusion polypeptides is fused to a sequence encoding a viral coat protein; and
   wherein the viral coat protein is encoded by gene 3 of the filamentous bacteriophage M13, fd or related species;
   (c) the progeny phage are exposed to trypsin capable of cleaving the protease-cleavable site, such that the cleavage of the protein encoded by gene 3 derived from the helper phage impairs the phage's ability to mediate infection, and
   (d) the phage progeny are propagated by infection in bacteria.

2. method comprising the steps of:
   (a) creating a library of phagemids encoding a repertoire of heterologous polypeptides;
   wherein sequence encoding the repertoire of heterologous polypeptides is fused to a sequence encoding a viral coat protein; and
   wherein the viral coat protein is encoded by gene 3 of the filamentous bacteriophage M13, fd or related species;
   (b) expressing the phagemids in bacteria in the presence of helper phage to produce phage progeny;
   wherein the helper phage is a filamentous bacteriophage M13, fd or related species;
   wherein the helper phage comprises a coat protein;
   wherein the coat protein is encoded by gene 3 of the filamentous bacteriophage M13, fd or related species; and
   wherein a protease-sensitive cleavage site is introduced between the second and third domain of the gene 3 protein;
   (c) subjecting the phage progeny to protease cleavage by trypsin;
   (d) infecting bacteria with the phage progeny of step (c); and
   (e) isolating the phagemids from the bacteria infected with the phage progeny.

* * * * *